US011071752B2

(12) United States Patent
La Francesca et al.

(10) Patent No.: US 11,071,752 B2
(45) Date of Patent: *Jul. 27, 2021

(54) ORGANS FOR TRANSPLANTATION

(71) Applicants: ABT Holding Company, Cleveland, OH (US); Houston Methodist Hospital, Houston, TX (US)

(72) Inventors: Saverio La Francesca, Houston, TX (US); Anthony E. Ting, Shaker Heights, OH (US); Robert J. Deans, Cleveland Heights, OH (US)

(73) Assignees: ABT Holding Company, Cleveland, OH (US); Houston Methodist Hospital, Houston, TX (US)

( * ) Notice: Subject to any disclaimer, the term of this patent is extended or adjusted under 35 U.S.C. 154(b) by 223 days.

This patent is subject to a terminal disclaimer.

(21) Appl. No.: 16/385,957

(22) Filed: Apr. 16, 2019

(65) Prior Publication Data

US 2019/0269725 A1 Sep. 5, 2019

Related U.S. Application Data

(63) Continuation of application No. 15/864,862, filed on Jan. 8, 2018, now Pat. No. 10,272,109, which is a continuation of application No. 14/252,364, filed on Apr. 14, 2014, now Pat. No. 9,861,660.

(60) Provisional application No. 61/811,525, filed on Apr. 12, 2013.

(51) Int. Cl.
*A61K 35/12* (2015.01)
*C12N 5/074* (2010.01)
*C12N 5/00* (2006.01)

(52) U.S. Cl.
CPC ............ *A61K 35/12* (2013.01); *C12N 5/0018* (2013.01); *C12N 5/0607* (2013.01); *C12N 2500/84* (2013.01); *C12N 2502/03* (2013.01)

(58) Field of Classification Search
CPC ............ C12N 2502/03; C12N 2500/84; C12N 5/0607; A61K 39/001; A61K 35/12; A61P 37/06

See application file for complete search history.

(56) References Cited

U.S. PATENT DOCUMENTS

| 5,197,985 | A | 3/1993 | Caplan et al. |
|---|---|---|---|
| 5,486,359 | A | 1/1996 | Caplan et al. |
| 5,736,396 | A | 4/1998 | Bruder et al. |
| 5,827,735 | A | 10/1998 | Young et al. |
| 5,906,934 | A | 5/1999 | Grande et al. |
| 6,090,625 | A | 7/2000 | Abuljadayel |
| 6,214,369 | B1 | 4/2001 | Grande et al. |
| 6,281,012 | B1 | 8/2001 | McIntosh |
| 6,328,960 | B1 | 12/2001 | McIntosh et al. |
| 6,368,636 | B1 | 4/2002 | McIntosh |
| 6,387,369 | B1 | 5/2002 | Pittenger et al. |
| 6,653,134 | B2 | 11/2003 | Prockop et al. |
| 6,685,936 | B2 | 2/2004 | McIntosh |
| 6,777,231 | B1 | 8/2004 | Katz et al. |
| 6,797,269 | B2 | 9/2004 | Mosca |
| 6,875,430 | B2 | 4/2005 | McIntosh |
| 7,015,037 | B1 | 3/2006 | Furcht et al. |
| 7,045,148 | B2 | 5/2006 | Hariri |
| 7,056,738 | B2 | 6/2006 | Prockop et al. |
| 7,229,827 | B2 | 6/2007 | Kim et al. |
| 7,311,905 | B2 | 12/2007 | Hariri |
| 7,491,388 | B1 | 2/2009 | McIntosh |
| 7,659,118 | B2 | 2/2010 | Furcht et al. |
| 7,838,289 | B2 | 11/2010 | Furcht et al. |
| 7,883,892 | B2 | 2/2011 | Verfaillie et al. |
| 7,927,587 | B2 | 4/2011 | Blazer et al. |
| 8,075,881 | B2 | 12/2011 | Verfaillie et al. |
| 8,147,824 | B2 | 3/2012 | Maziarz et al. |
| 8,192,348 | B2 | 6/2012 | Tranquillo et al. |
| 8,252,280 | B1 | 8/2012 | Verfaillie et al. |
| 8,268,619 | B2 | 9/2012 | Giacomello et al. |
| 8,409,859 | B2 | 4/2013 | Verfaillie et al. |
| 8,426,200 | B2 | 4/2013 | Verfaillie et al. |
| 8,580,249 | B2 | 11/2013 | Blazer et al. |
| 8,609,406 | B2 | 12/2013 | Subramanian et al. |

(Continued)

FOREIGN PATENT DOCUMENTS

| EP | 2241617 A1 | 10/2010 |
|---|---|---|
| EP | 2377542 A2 | 10/2011 |

(Continued)

OTHER PUBLICATIONS

Reply in case U.S. Appl. No. 14/252,364 recieved Jul. 31, 17, 12 pages (Year: 2017).*
Dean Declaration in U.S. Appl. No. 14/252,364 on Jul. 31, 17, 24 pages (Year: 2017).*
Wu et al., Generation of Pancreatic β Cells From Mesenchymal Stem Cells to Treat Type 1 Diabetes, OA Stem Cells, Mar. 22, 2014 ; 2 (1) : 5.
Guo et al., Differentiation of Mesenchymal Stem Cells Into Dopaminergic Neuron-like Cells in Vitro, Biomedical and Environmental Sciences, 18, 36-42 (2005).

(Continued)

*Primary Examiner* — Thane Underdahl
(74) *Attorney, Agent, or Firm* — Tarolli, Sundheim, Covell & Tummino LLP

(57) ABSTRACT

The invention provides methods and compositions that improve the success of organ transplantation. The methods and compositions are directed to exposing a desired organ to stem cells prior to, during, and/or after transplantation. In one embodiment, the stem cells reduce the deleterious effects of ischemia on an organ designated to be harvested for transplantation or that has been harvested for transplantation. In another embodiment in which an organ designated for transplantation is perfused ex vivo, the method involves reducing ischemic reperfusion injury by perfusing the organ with a medium that contains stem cells.

19 Claims, 10 Drawing Sheets

Specification includes a Sequence Listing.

(56) References Cited

U.S. PATENT DOCUMENTS

| | | | |
|---|---|---|---|
| 8,609,412 B2 | 12/2013 | Panoskaltsis-Mortari et al. |
| 9,005,964 B2 | 4/2015 | Verfaillie et al. |
| 9,057,051 B2 | 6/2015 | Pauwelyn et al. |
| 9,090,878 B2 | 7/2015 | Sancho-Bru et al. |
| 9,388,388 B2 | 7/2016 | Verfaillie et al. |
| 9,447,380 B2 | 9/2016 | Subramanian et al. |
| 9,526,747 B2 | 12/2016 | Verfaillie et al. |
| 9,617,513 B2 | 4/2017 | Young et al. |
| 9,644,182 B2 | 5/2017 | Baksh et al. |
| 9,700,601 B2 | 7/2017 | Blazer et al. |
| 9,764,044 B2 | 9/2017 | Verfaillie et al. |
| 9,777,258 B2 | 10/2017 | Sancho-Bru et al. |
| 9,789,136 B2 | 10/2017 | Furcht et al. |
| 9,808,485 B2 | 11/2017 | Maziarz et al. |
| 9,861,660 B2 | 1/2018 | LaFrancesca et al. |
| 9,937,208 B2 | 4/2018 | Mays |
| 9,962,407 B2 | 5/2018 | Deans et al. |
| 9,974,809 B2 | 5/2018 | Furcht et al. |
| 9,974,810 B2 | 5/2018 | Furcht et al. |
| 9,974,811 B2 | 5/2018 | Furcht et al. |
| 10,006,004 B2 | 6/2018 | Furcht et al. |
| 10,117,900 B2 | 11/2018 | Mays et al. |
| 10,160,948 B2 | 12/2018 | Young et al. |
| 10,226,485 B2 | 3/2019 | Furcht et al. |
| 10,253,297 B2 | 4/2019 | Hu et al. |
| 10,272,109 B2 | 4/2019 | LaFrancesca et al. |
| 2001/0033834 A1 | 10/2001 | Wilkison et al. |
| 2001/0046489 A1 | 11/2001 | Habener et al. |
| 2002/0061587 A1 | 5/2002 | Anversa |
| 2002/0164794 A1 | 11/2002 | Wernet |
| 2003/0003090 A1 | 1/2003 | Prockop et al. |
| 2003/0032179 A1 | 2/2003 | Hariri |
| 2003/0059414 A1 | 3/2003 | Ho et al. |
| 2004/0033214 A1 | 2/2004 | Young et al. |
| 2004/0235165 A1 | 11/2004 | Prockop et al. |
| 2005/0152995 A1 | 7/2005 | Chen |
| 2005/0169896 A1 | 8/2005 | Li et al. |
| 2005/0239897 A1 | 10/2005 | Pittenger et al. |
| 2005/0255588 A1 | 11/2005 | Young et al. |
| 2005/0283844 A1 | 12/2005 | Furcht et al. |
| 2006/0177925 A1 | 8/2006 | Rosenberg et al. |
| 2006/0228798 A1 | 10/2006 | Verfaillie et al. |
| 2007/0010484 A1 | 1/2007 | Schwartz |
| 2007/0104697 A1 | 5/2007 | Wilkison |
| 2008/0095749 A1 | 4/2008 | Aggarwal |
| 2008/0113434 A1 | 5/2008 | Davies et al. |
| 2008/0181865 A1 | 7/2008 | Schaebitz |
| 2008/0194021 A1 | 8/2008 | Mays |
| 2008/0194024 A1 | 8/2008 | Mays |
| 2008/0213227 A1 | 9/2008 | Aggarwal |
| 2008/0311084 A1 | 12/2008 | Verfaillie et al. |
| 2008/0317740 A1 | 12/2008 | Blazar et al. |
| 2009/0104159 A1 | 4/2009 | Prosper et al. |
| 2010/0008890 A1 | 1/2010 | Mays et al. |
| 2010/0172885 A1 | 7/2010 | Pittenger |
| 2010/0239542 A1 | 9/2010 | Young et al. |
| 2010/0239543 A1 | 9/2010 | Young et al. |
| 2011/0020292 A1 | 1/2011 | Van't Hof |
| 2011/0020293 A1 | 1/2011 | Woda et al. |
| 2011/0027238 A1 | 2/2011 | Aggarwal |
| 2011/0064701 A1 | 3/2011 | Young et al. |
| 2011/0111492 A1 | 5/2011 | Hu et al. |
| 2011/0171659 A1 | 7/2011 | Furcht et al. |
| 2011/0177595 A1 | 7/2011 | Furcht et al. |
| 2011/0206647 A1 | 8/2011 | Woda et al. |
| 2011/0212069 A1 | 9/2011 | Hamilton et al. |
| 2011/0293578 A1 | 12/2011 | Busch et al. |
| 2011/0305638 A1 | 12/2011 | Ting et al. |
| 2011/0311496 A1 | 12/2011 | Pittenger |
| 2011/0318313 A1 | 12/2011 | Cox, Jr. et al. |
| 2011/0318314 A1 | 12/2011 | Aggarwal |
| 2011/0318315 A1 | 12/2011 | Aggarwal |
| 2012/0009674 A1 | 1/2012 | Mays |
| 2012/0021019 A1 | 1/2012 | Giacomello et al. |
| 2012/0219572 A1 | 8/2012 | Prockop et al. |
| 2012/0308531 A1 | 12/2012 | Pinxteren et al. |
| 2013/0129686 A1 | 5/2013 | Highfill et al. |
| 2014/0037596 A1 | 2/2014 | Woda et al. |
| 2014/0134137 A1 | 5/2014 | Van't Hof |
| 2014/0186307 A1 | 7/2014 | Busch et al. |
| 2014/0186954 A1 | 7/2014 | Pauwelyn et al. |
| 2014/0234267 A1 | 8/2014 | Panoskaltsis-Mortari et al. |
| 2014/0242629 A1 | 8/2014 | Woda et al. |
| 2014/0295442 A1 | 10/2014 | Hamilton et al. |
| 2014/0322135 A1 | 10/2014 | Roobrouck et al. |
| 2015/0093364 A1 | 4/2015 | Busch et al. |
| 2015/0118193 A1 | 4/2015 | Maziarz et al. |
| 2015/0267167 A1 | 9/2015 | Furcht et al. |
| 2016/0069903 A1 | 3/2016 | Lakadamyali et al. |
| 2016/0282336 A1 | 9/2016 | Hamilton et al. |
| 2016/0326494 A1 | 11/2016 | Cunha et al. |
| 2017/0022472 A1 | 1/2017 | Pinxteren et al. |
| 2017/0209493 A1 | 7/2017 | Young et al. |
| 2018/0055881 A1 | 3/2018 | Maziarz et al. |
| 2018/0110806 A1 | 4/2018 | Furcht et al. |
| 2018/0250342 A1 | 9/2018 | Mays |
| 2018/0272000 A1 | 9/2018 | Verfaillie et al. |
| 2018/0296609 A1 | 10/2018 | Mays et al. |
| 2018/0311287 A9 | 11/2018 | Cox et al. |
| 2018/0318346 A1 | 11/2018 | Deans et al. |
| 2019/0048314 A1 | 2/2019 | Woda et al. |
| 2019/0233794 A1 | 8/2019 | Hu et al. |

FOREIGN PATENT DOCUMENTS

| | | |
|---|---|---|
| WO | WO 96/23870 | 8/1996 |
| WO | WO 99/16863 | 4/1999 |
| WO | WO 99/35243 | 7/1999 |
| WO | 99/47163 A2 | 9/1999 |
| WO | WO 01/04268 | 1/2001 |
| WO | WO 01/08691 | 2/2001 |
| WO | WO 01/21766 | 3/2001 |
| WO | WO 01/21767 | 3/2001 |
| WO | WO 02/08388 | 3/2001 |
| WO | WO 01/62950 | 8/2001 |
| WO | WO 02/34890 | 5/2002 |
| WO | WO 04/87896 | 10/2004 |
| WO | WO 08/021196 | 2/2008 |
| WO | WO 08/109674 | 9/2008 |
| WO | WO 10/149597 | 12/2010 |
| WO | WO2017062035 | 4/2017 |

OTHER PUBLICATIONS

Piccinato et al., High OCT4 and Low p16INK4A Expressions Determine in Vitro Lifespan of Mesenchymal Stem Cells, Stem Cells International, vol. 2015, Article ID 369828, 11 pages.

Decision on Motions; Patent Interference No. 105,953 SGL, Tech Center 1600; filed Sep. 26, 2014.

Delves, Peter, Human Leukocyte Antigen (HLA) System, Merck Manuals Professional Edition, last edited in 2014.

DifferenceBetween.net "Difference Between MHC and HLA" uploaded Mar. 25, 2012.

Riekstina, et al., Embryonic Stem Cell Marker Expression Pattern in Human Mesenchymal Stem Cells Derived from Bone Marrow, Adipose Tissue, Heart and Dermis, Stem Cell Rev and Rep (2009) 5:378-386.

Rosland, et al., Long-term Cultures of Bone Marrow-Derived Human Mesenchymal Stem Cells Frequently Undergo Spontaneous Malignant Transformation, Cancer Res 2009; 69:(13) Jul. 1, 2009.

Renner, et al., Feasibility of continuous ex vivo kidney perfusion with mesenchymal stem cells to prevent ischemia-reperfusion injury in mice, Transplant International, May 4, 2012, vol. 25.

Jo, C.H., et al., Fetal mesenchymal stem cells derived from human umbilical cord sustain primitive characteristics during extensive expansion. Cell Tissue Res, Oct. 22, 2008, vol. 334, No. 3, pp. 423-433.

Eggenhofer, et al., Heart grafts tolerized through third-party multipotent adult progenitor cells can be retransplanted to secondary hosts with no immunosuppression, Stem Cells Transl Med, Jul. 8, 2013, vol. 2, No. 8, pp. 595-606.

(56) References Cited

OTHER PUBLICATIONS

Yanjie, et al., Effects of Notch-I Signalling Pathway on Differentiation of Marrow Mesenchymal Stem Cells Into Neurons In Vitro, NeuroReport, 2007, pp. 1443-1447, vol. 18.
Karaöz, et al., A Comprehensive Characterization Study of Human Bone Marrow MSCs with an Emphasis on Molecular and Ultrastructural Properties, J. Cell. Physiol., 2011, pp. 1367-1382, vol. 226.
Guillot, et al., Human First-Trimester Fetal MSC Express Pluripotency Markers and Grow Faster and Have Longer Telomeres Than Adult MSC, Stem Cells, 2007, pp. 646-654, vol. 25.
Greco, et al., Functional Similarities Among Genes Regulated by Oct4 in Human Mesenchymal and Embryonic Stem Cells, Stem Cells, 2007, pp. 3143-3154, vol. 25.
Xiao, et al., Transplantation of a Novel Cell Line Population of Umbilical Cord Blood Stem Cells Ameliorates Neurological Deficits Associated with Ischemic Brain Injury, Stem Cells & Dev., 2005, pp. 722-733, vol. 14.
Zhang, et al., Separation, Purification and Identification of Rat Bone Marrow Mesenchymal Stem Cells, Engineering Science (Res. Rep.), Jul. 2007, vol. 9(7) (English Translation).
Shetty, et al., Comparison of Proliferative and Multilineage Differentiation Potentials of Cord Matrix, Cord Blood, and Bone Marrow Mesenchymal Stem Cells, Asian J. Transfus. Sci., Jan. 2010, pp. 14-24, vol. 4(1).
Zuk, Patricia A., The Intracellular Distribution of the ES Cell Totipotent Markers OCT4 and Sox2 in Adult Stem Cells Differs Dramatically According to Commercial Antibody Used, J. Cell. Biochem., 2009, pp. 867-877, vol. 106.
Ting, et al., Allogeneic Stem Cell Transplantation for Ischemic Myocardial Dysfunction, Curr. Opin. Organ Transplant, 2012, pp. 675-680, vol. 17.
Mays, et al., Development of Adult Pluripotent Stem Cell Therapies for Ischemic Injury and Disease, Expert Opin. Biol. Ther., 2007, 173-184, vol. 7(2).
Casiraghi, et al., Pretransplant Infusion of Mesenchymal Stem Cells Prolongs the Survival of a Semiallogeneic Heart Transplant Through the Generation of Regulatory T Cells, J. Immunol., 2008, pp. 3933-3946, vol. 181.
Ryu, et al., Molecular Imaging of the Paracrine Proangiogenic Effects of Progenitor Cell Therapy in Limb Ischemia, Circulation, 2013, pp. 710-719, vol. 127(6).
Popp, et al., Safety and Feasibility of Third-Party Multipotent Adult Progenitor Cells for Immunomodulation Therapy After Liver Transplantation—A Phase I Study (MISOT-I), J. Transl. Med., Jul. 28, 2011, 9:124. doi: 10.1186/1479-5876-9-124.
Form 892, Issued in U.S. Appl. No. 13/071,801, filed Sep. 15, 2016.
Form 892, Issued in U.S. Appl. No. 13/071,801, filed Mar. 5, 2019.
Form 892, Issued in U.S. Appl. No. 13/071,801, filed May 3, 2018.
Form 892, Issued in U.S. Appl. No. 13/062,343, filed Apr. 11, 2018.
Form 892, Issued in U.S. Appl. No. 14/252,364, filed May 5, 2016.
Form 892, Issued in U.S. Appl. No. 14/252,364, filed Feb. 3, 2017.
Form 892, Issued in U.S. Appl. No. 15/864,862, filed Dec. 13, 2018.
Cambrex specimens, "Poistics Human Mesenchymal Stem Cell Systems," Cambrex BioScience Walkersviile, Inc. (2005).
Prockop, D., "Marrow stromal cells as stem cells for nonhematopoietic tissues" Science; 276:71-74 (1997).
Bjornson et al., "Turning brain into blood: a hematopoletic fate adopted by adult neural stem cells in vivo" Science: 263:534-537 (1999).
Reyes et al., "Purification and ex vivo expansion of postnatal human marrow mesodermal progenitor cells" Blood; 98:2615-25 (2001).
Bouwens, L., "Transdifferentiation versus stem cell hypothesis for the regeneration of islet beta-cells in the pancreas" Microscopy Research and Technique; 43:332-336 (1998).
Reyes et al., "Origin of endothelial progenitors in human postnatal bone marrow" J. Clin. Invest.; 109:1-10 (2002).
Reyes et al., "Characterization of multilineage mesodermal progenitor cells in adult marrow" Abstract No. 124, American Society for Hematology (2001).
Reyes et al., "Turning marrow into brain: generation of glial and neuronal cells from adult bone marrow mesenchymal stem cells" Abstract No. 1676, American Society for Hematology (2001).
Reyes et al., "Skeletal smooth and cardiac muscle differentiation from single adult marrow derived mesodermal progenitor cells" Abstract No. 2610, American Society for Hematology (2001).
Reyes et al., "In vitro and in vivo characterization of neural cells, derived from mesenchymal stem cells" Abstract 2126, American Society for Hematology (2001).
Reyes et al., "Endothelial cells generated from human marrow derived mesenchymal stem cells (MSC)" Abstract No. 2276, American Society for Hematology (2001).
Zhao et al., "Immunohistochemical identification of muitipotent adult progenitor cells from human bone marrow after transplantation into the rat brain" Brain Res Brain Res Protoc; 11:38-45 (2003).
Jiang et al., "Multipotent progenitor cells can be isolated from postnatal murine bone marrow, muscle, and brain" Exp. Hematol.; 30:896-904 (2002).
Jiang et al., "Pluripotency of mesenchymal stem cells derived from adult marrow" Nature; 418:41-49 (2002).
Schwartz, R., "Multipotent adult progenitor cells from bone marrow differentiate into hepatocyte-like cells" J Clin Invest.; 109:1291~1302 (2002).
Zhao et al., "Human bone marrow stem cells exhibit neural phenotypes and ameliorate neurological deficits after grafting into the ischemic brain of rats" Exp Neurol; 174:11-20 (2002).
Lamming et al., "Spontaneous circulation of myeloid-lymphoid-initiating cells and SCID-repopulating cells in sickle cell crisis" J. Clin. Invest.; 111:811-819 (2003).
Qi et al., "Identification of genes reponsible for osteoblast differentiation from human mesodermal progenitor cells" Nat. Acad. Sci. USA; 100:3305-3310 (2003).
Verfaillie, C. "Investigator Profile" Journal of Hematotherapy and Stem Cell Research; 11:441-444 (2002).
Verfaillie et al., "Stem cells: hype and reality" Hematology (Am Soc Hematol Educ Program); 369-391 (2002).
Verfaille, C., "Optimizing hematopoietic stem cell engraftment: a novel role for thrombopoeitin" J. Clin. Invest.; 110:303-304 (2002).
Liu et al., "Myeloid-lymphoid-initiating cells (ML-IC) are highly enriched in the rhodamine-C-Kit(+) CD33(−)CD38(−) fraction of umbilical cord CD34(+)" Exp. Hematol.; 30:582-589 (2002).
Lewis et al., "Multi-lineage expansion potential of primitive hematopoietic progenitors: superiority of umbilical cord blood compared to mobilized peripheral blood" Exp. Hematol.: 28:1087-1095 (2002).
Verfaillie, C.M., "Meeting Report on an NHLBI Workshop on ex vivo expansion of stem cells, Jul. 29, 1999, Washington D.C. National Heart Lung and Blood Institute" Exp. Hematol.; 26:361-364 (2000).
Punzel et al., "The myeloid-lymphoid initiating cell (ML-IC) assay assesses the fate of multipotent human progenitors in vitro" Blood; 93:3750-3756 (1999).
Roy et al., "Expression and function of cell adhesion molecules on fetal liver, cord blood and bone marrow hematopoietic progenitors: implications for anatomical localization and developmental stage specific regulation of hematopoiesis" Exp. Hematol.; 27:302-312 (1999).
Miller et al., "Ex vivo culture of CD34+/Lin-/DR-cells in stroma-derived soluble factors, interleukin-3, and macrophage inflammatory protein-1 alpha maintains not only myeloid but also lymphoid progenitors in a novel switch culture asssay" Blood; 15:4516-4522 (1998).
Verfaillie, C., "Stem cells in chronic myelogenous Leukemia" Hematol. Oncol. Clin. North Am.; 11:1079-1114 (1997).
Prosper et al., "Phenotypic and functional characterization of long-term culture-initiating cells present in peripheral blood progenitor collections of normal donors treated with granulocyte colony-stimulating factor" Blood; 15:2033-2042 (1996).
Lodie et al., "Systematic analysis of reportedly distinct populations of multipotent bone marrow-derived stem cells reveals a lack of distinction" Tissue Engineering; 8:739-751 (2002).
Pagen Westphal, S., "Adult bone marrow eyed as source of stem cells" Boston Globe, Jan. 24, 2002.

(56) References Cited

OTHER PUBLICATIONS

Pagen Westphal, S., "Ultimate stem cell discovered" New Scientist, Jan. 23, 2002.
Wade et al., "Scientists herald a versatile adult cell" The New York Times on the Web, Jan. 25, 2002.
Rosford et al., "The octamer motif present in the Rex-1 promoter binds Oct-1 and Oct-3 expressed by EC cells and ES cells" Biochem. Biophys. Res. Comm.; 203:1795-1802 (1994).
Rosner et al., "Oct-3 is a maternal factor required for the first mouse embryonic division" Cell; 64:1103-1110 (1991).
Pittenger et al., "Multilineage potential of adult human mesenchymal stem cells"; Science; 284:143-147 (1999).
Ben-Shushan et al., "Rex1, a gene encoding a transcription factor expressed in the early embryo, is regulated via Oct-3/4 and Oct-6 binding to and octamer site and a novel protein, R ox-1, binding to an adjacent site" Mol. Cell Biol.; 18:1866-1878 (1998).
Reyes et al., "Characterization of multipotent adult progenitor cells, a subpopulation of mesenchymal stem cells" Annals of the New York Academy of Science; 938:231-235 (2001).
Anjos-Afonso and Bonnet, "Nonhematopoletic/endothelial SSE-1+ cells define the most primitive progenitors in the adult murine bone marrow mesenchymal compartment" Blood; 109:1298-1306 (2007).
Bertani et al., "Neurogenic potential of human mesenchymal stem cells revisited: analysis by immunostaining, time-lapse video and microarray" J Cell Sci.; 118:3925-36 (2005).
Bodnar et al., "Extension of life-span by introduction of telomerase into normal human cells" Science; 279:349-352 (1998).
Horwitz et al., "Clarification of the nomenclature for MSC: the international society for ceullalar therapy position paper" Cytotherapy; 7:393-395 (2005).
Lu et al., "Induction of bone marrow siromal cells to neurons: differentiation, transdifferentiation, or artifact" J Neurosci Res; 77:174-91 (2004).
Neuhuber et al., "Reevaluation of in vitro differentiation protocols for bone marrow stromal cells: disruption of actin cyloskeleton induces rapid morphological changes and mimics neuronal phenotype" J Neurosci Res; 77:192-204 (2004).
Simonsen et al., "Telomerase expression extends the proliferative life-span and maintains the osteogenic potential of human bone marrow stromal cells" Nature Biotechnology; 20:592-596 (2002).
Zimmerman et al., "Lack of telomerase activity in human mesenchymal stem cells" Leukemia; 17:1146-1149 (2003).
Izadpanah et al., "Biologic properties of mesenchymal stem cells derived from bone marrow and adipose tissue" Journal of Cellular Biochemistry; 99:1285-1297 (2006).
Long et al., "Neural cell differentiation In vitro from adult human bone marrow mesenchymal stem cells" Stem Cells and Development; 14:65-69 (2005).
Moriscot et al., "Human bone marrow mesenchymal stem cell can express insulin and key transcription factors of the endocrine pancreas developmental pathway upon genetic and/or microenvironmental manipulation in vitro" Stem Cells; 23:594-604 (2005).
Sanchez-Ramos et al., "Adult bone m arrow stromal cells differentiate into neural cells In vitro" Exp. Neurol.; 164:247-56 (2000).
Eglitis et al., "Hematopoietic cells differentiate into both microglia and macroglia in the brain of adult mice" Proc. Natl. Acad. Sci. USA; 94:4080-85 (1997).
Kopen et al., "Marrow stromal cells migrate throughout forebrain and cerebellum, and they differentiate into astrocytes after injection into neonatal mouse brains" Proc. Natl. Acad. Sci. USA; 96:10711-16 (1999).
Lagasse et al., "Purified hematopoietic stem cells can differentiate into hepatoctyes in vivo" Nature Medicine; 8:1229-1234 (2000).
Wang, X. et al., "Cell fusion is the principal source of bone-marrow-derived hepatocytes" Nature; 422:897-901 (2003).
Giles, J., "The trouble with replication" Nature, 422:344-347 (2006).
Verfaillie, C.M., Multipotent adult progenitor cells: an update: Novartis Found Symp., 254:55-65 (2005).

Aldhous et al., "Fresh questions on stem cell findings" New Scientist, Mar. 21, 2007.
Brazelton et al., "From marrow to brain: expression of neuronal phenotypes in adult mice" Science; 290:1775-9 (2000).
Clarke et al., "Generalized potential of adult nerual stem cells" Science; 288: 1660-3 (2000).
Johansson et al., "Neural stem cells in the adult human brain" Exp. Cell. Res.: 253:733-6 (1999).
Mezey et al., "Turning blood intro brain: cells bearing neuronal antigens generated in vivo from bone marrow" Science; 290:1779-82 (2000).
Morshead et al., "Hematopoietic competence is a rare property of neural stem cells that may depend on genetic and epigenetic alterations" Nat. Med.; 8:268-73 (2002).
Petersen et al., "Bone marrow as a potential source of hepatic oval cells" Science; 284:1168-70 (1999).
Scintu et al., "Differentiation of human bone marrow stem cells into cells with a neural phenotype: diverse effects of two specific treatments" BMC Neurosci.; 7:14 (2006).
U.S. Patent and Trademark Office, Office Action dated Jun. 24, 2005 in related U.S. Appl. No. 10/040,757.
U.S. Patent and Trademark Office. Office Action and 892 dated Jun. 27, 2008 in related U.S. Appl. No. 10/467,963.
U.S. Patent and Trademark Office, Office Action dated Oct. 15, 2009 in related U.S. Appl. No. 10/467,963.
U.S. Patent and Trademark Office, Office Action and 892 dated Apr. 7, 2008 in related U.S. Appl. No. 11/151,689.
U.S. Patent and Tradmark Office, Office Action dated Jan. 4, 2006 in related U.S. Appl. No. 11/238,234.
U.S. Patent and Trademark Office, Office Action dated Aug. 29, 2006 in related U.S. Appl. No. 11/238,234.
U.S. Patent and Trademark Office, Office Action and 892 dated Apr. 3, 2007 in related U.S. Appl. No. 11/236,234.
U.S. Patent and Trademark Office, Office Action dated Oct. 7, 2008 in related U.S. Appl. No. 11/238,234.
Communication and 1449, filed Oct. 2, 2007 in related U.S. Appl. No. 11/238,234, and supplemental 1449 submitted on Oct. 4, 2007.
Information Disclosure Statement, Second Communication and PTO/SB/08b, filed Dec. 24, 2008 in related U.S. Appl. No. 11/238,234.
Sun et al., "Autologous Transplantation of Adipose-Derived Mesenchymal Stem Cells Markedly etc." Journal of Translation Medicine, Jul. 22, 2011 vol. 8, No. 118, pp. 1-13.
International Search Report for Application No. PCT/US2014/034015 dated Aug. 29, 2014.
Prockop et al., "Mesenchymal Stem/Stromal Cells (MSCs): Role as Guardians of Inflammation", Molecular Therapy, Oct. 18, 2011 (Oct. 18, 2011), vol. 20; No. 1, pp. 14-20.
Evans, M.J., et al. Nature (1981); vol. 292; pp. 154-156.
Martin, G.R. Proc. Natl. Acad. Sci. USA (1981); vol. 78, No. 12; pp. 7634-7638.
Woodbury, D., et al. J Neurosci Res (2000); vol. 61; pp. 364-370.
Lee, K-D., et al. Hepatology (2004); vol. 40; pp. 1275-1284.
Verfaillie, C.M. Letter to the editor. Exp Hemat (2007).
Tai, M.H., et al. Oct4 expression in adult human stem cells: evidence in support of the stem cell theory of carcinogenesis. Carcinogenesis (2005) vol. 26, pp. 495-502.
Public Statement from the University of Minnesota; pp. 1-2.
Kolf, C.M., et al. Review Mesenchymal stromal cells: Arthritis Research & Therapy, (2007) vol. 9:204 pp. 1-10.
Liedtke, S., eat al. Oct4 expression revisited; potential pitfalls for data misinterpretation in stem cell research. Biol. Chem., (2008) vol. 389, pp. 845-850.
Atlasi, Y., et al. Oct4 Spliced Variants are Differentially Expressed in Human Pluripotent and Nonpluripotent Cells. Stem Cells, (2008) vol. 26, pp. 3068-3074.
Roche, S., et al. Oct-4, Rex-1, and Gata-4 expression in human MSC increase the differentiation efficiency but not hTERT expression. J. Cell. Biochem. (2007) vol. 101, pp. 271-280.
Tondreau, T., et al. Mesenchymal stem cells derived from CD133-positive cells in mobilized peripheral blood and cord blood: proliferation, Oct4 expression, and plasticity. Stem Cells (2005) vol. 23, pp. 1105-1112.

(56) References Cited

OTHER PUBLICATIONS

Takeda, J., et al. Human Oct3 gene family: cDNA sequences, alternative splicing, gene organization chromosomal location, and expression at low levels in adult tissues. Nucleic Acids Research (1992) vol. 20, No. 17, pp. 4613-4620.

Brehm, A., et al. The Carboxy-Terminal Transactivation Domain of Oct-4 Acquires Cell Specificity through the POU Domain. Mol. Cell. Biol. (1997) vol. 17, No. 1, pp. 154-162.

Mahmood, A. et al. Treatment of Traumatic Brain Injury in Adult Rats with Intravenous Administration of Human Bone Marrow Stromal Cells. Neurosurgery (2003) vol. 53, pp. 697-703.

Woodbury, D., et al. Adult Rat and Human Bone Marrow Stromal Cells Differentiate into Neurons. J of Neuroscience Research (2000), vol. 61, pp. 364-370.

Digirolamo, C.M., et al. Propagation and senescence of human marrow stromal cells in culture: British Journal of Haematology (1999) vol. 107, pp. 275-281.

Ohtaki, H., et al. Sterm/progenitor cells from bone marrow decrease neuronal death in global ischemia by modulation of inflammatory/immune responses, PNAS (2008) vol. 105, No. 38, pp. 14638-14543.

Dirk Van Raemdonck et al., "Machine parfusion in organ transplantation", Current Opinion in Organ Transplantation, vol. 18, No. 1, Feb. 1, 2013 (Feb. 1, 2013), pp. 24-33.

European Search Report for Application No. 14782499.9, dated Nov. 25, 2016.

Ong, Shin-Yeu, et al., Hepatic Differentiation Potential of Commercially Available Human Mesenchymal Stem Cells, Tiss. Eng., 2006, pp. 3477-3485, vol. 12(12).

Jiang, Wenqi, et al., Cancer Biotherapy, Guangzhou Science & Technology Press, Chapter 6 Stem Cell Therapy, Section 2 Mesenchymal Stem Cells, Apr. 1, 2006, China (With English Translation Attached).

Liu, Bin, Editor, Histology and Embryology, 1st Ed., Chap. 5(IV) Blood and Hemopoiesis, Peking University Medical Press, May 2005, China (With English Translation Attached).

Pei, Xuetao, Editor, Stem Cell Biology, 1st Ed., 17.2.2 Mesenchymal Stem Cells (MSCs), Jul. 2003, China (With English Translation Attached).

Li, Jing-Yuan et al., Telomerase Activity of Human Bone Marrow Mesenchymal Stem Cells, J. Zhejiang Univ. (Med Sci 2004 Nov. 2004, 33(6):481-485, China.

* cited by examiner

ORGANS FOR TRANSPLANTATION

SEQUENCE LISTING

The instant application contains a sequence listing which has been submitted electronically in ASCII format and is hereby incorporated by reference in its entirety. Said ASCII copy, created on Apr. 8, 2014, is named ATH-022234USORD_SL.txt and is 7,517 bytes in size.

FIELD OF THE INVENTION

The field of the invention is organ transplantation and providing methods and compositions that improve the success of organ transplantation. The methods and compositions are directed to exposing a desired organ, prior to or during transplantation, to stem cells. In one embodiment, the stem cells reduce the deleterious effects of ischemia on an organ designated to be harvested for transplantation or that has been harvested for transplantation. In another embodiment, the organ is a lung. In a further embodiment in which an organ designated for transplantation is perfused ex vivo, the method involves reducing ischemic reperfusion injury by perfusing the organ with a medium that contains stem cells.

BACKGROUND OF THE INVENTION

Organ transplantation represents the preparation and harvesting of an organ from a donor or a donor site (if the donor and recipient are the same), and the implantation, maintenance and/or use of the organ into or by the recipient of the donated organ. It has been estimated that there are more than 50,000 organ transplants performed per year in the major healthcare markets (e.g., U.S., Europe and Japan), and that there are more than 170,000 patients on waiting lists for organ transplants. Demand for healthy organs significantly outstrips the supply.

A major challenge in organ transplantation has been transplant rejection, which can lead to significant complications in organ function or to transplant failure. In general, this has been addressed through the matching of donors and recipients who have highly similar serotypes, and through the use of immunosuppressive drugs to manage the immunological response underlying transplant rejection.

Another major challenge has been preservation of organ viability prior to and during the implantation procedure. The removal, storage and transplantation of an organ may profoundly affect the internal structure and function of the organ and can influence significantly the degree to which the return of normal organ function is delayed or prevented after transplantation is completed. Such organ injury occurs primarily as a result of ischemia and hypothermia, but may also be related to reperfusion of the organ ex vivo or during implantation. Techniques for organ preservation, including ex vivo perfusion, serve to minimize this damage to promote optimal graft survival and function. But, even with these techniques, the organ health will decline is many cases, affecting transplantation outcome, and in some cases, the decline is so significant that the donated organs are rejected prior to transplantation as non-viable.

A technology that addresses these important challenges in organ transplantation should have a substantial impact on patient quality of life and survival, and on the treatment of the complications associated with transplantation.

SUMMARY OF THE INVENTION

The invention provides a method comprising transplanting an organ that has been exposed to exogenous stem cells prior to, during, and/or after transplantation. Exposure to the stem cells can improve the probability of a successful organ transplantation. Accordingly, the invention is directed to the following embodiments.

In one embodiment, the method may involve tolerizing the organ by contacting the organ with exogenous stem cells prior to, during, and/or after transplantation. By tolerizing the organ, that organ is better prepared to be accepted by a recipient without significant immunological interference. Tolerization can be achieved, for example, by the induction of T-regulatory cells in the organ (see, e.g., Eggenhofer et al., *Stem Cells Translation Medicine* 2013; 2:000-000).

In one embodiment, the invention is directed to a method to reduce injury in an organ ex vivo by contacting the organ with a medium that contains exogenous stem cells prior to, during, and/or after transplantation.

In one embodiment, the injury occurs as a result of ischemic reperfusion injury.

In one embodiment, the method is directed to reducing general tissue or cell degradation in the organ to be transplanted. This may result from factors including, but not limited to, ischemia, hypothermia and reperfusion. Accordingly, in one embodiment, the invention is directed to reducing injury as a result of one or more of these events. Such events may be caused, at least in part, by one or a combination of the following: (1) immunomodulation of TH1 T-cells to TH2 T-cells; (2) immunomodulation of M1 macrophages to M2 macrophages (e.g., causing a shift from a pro-inflammatory response to an anti-inflammatory response); (3) inhibiting the infiltration of neutrophils (e.g., by reducing the cell surface receptors); (4) shifting neutrophils from being pro-inflammatory to anti-inflammatory; and (5) cytoprotection or anti-apoptotic effects generated by the exogenous stem cells.

The events described herein may result in inflammation, other immunological response, cytokine production, cell apoptosis, and other events that affect the viability of an organ and suitability for transplantation. Accordingly, in one embodiment, the invention is directed to reducing the deleterious effects of these events by administering exogenous stem cells to an organ that is subject to these events or in which these events have already occurred.

Examples of events that may result in inflammation, other immunological response, cytokine production, cell apoptosis, and other events that affect the viability of an organ and suitability for transplantation can include, but are not limited to, those associated with endothelial response, reactive oxygen species, complement, and leukocytes. Events associated with endothelial response can include, but are not limited to, expression of certain pro-inflammatory gene products (e.g., leukocyte adhesion molecules, cytokines) and/or bioactive agents (e.g., endothelin, thromboxane $A_2$) and/or repression of other "protective" gene products (e.g., constitutive nitric oxide synthase, thrombomodulin) and/or bioactive agents (e.g., prostacyclin, nitric oxide). Events associated with reactive oxygen species (e.g., (O2-), (OH—), (HOCl), ($H_2O_2$), and nitric oxide-derived peroxynitrite) can include, but are not limited to, direct damage to cellular membranes by lipid peroxidation, stimulating leukocyte activation and chemotaxis by activating plasma membrane phospholipase A2 to form arachidonic acid (thromboxane A2 and leukotriene B4), and/or increasing leukocyte activation, chemotaxis, and leukocyte-endothelial adherence after ischemic reperfusion. Events associated with complement activation, such as C3a, C5a, iC3b, C5b9 (C5a is most potent) can include, but are not limited to, formation of several pro-inflammatory mediators that alter vascular homeostasis by, e.g., compromising blood flow to an ischemic organ by altering vascular homeostasis and increasing leukocyte-endothelial adherence. Events associated with leukocytes can include, but are not limited to, leukocyte activation, chemotaxis, leukocyte-endothelial cell adhesion and transmigration, which may further lead to mechanical obstruction, as leukocytes release toxic ROS, proteases, and elastases, resulting in increased microvascular permeability, edema, thrombosis, and parenchymal cell death.

In one embodiment, the organ is selected from the group including, but not limited to, lung, kidney, heart, liver, pancreas, thymus, gastrointestinal tract and composite allografts, such as limbs, faces and the like, and tissues including, but not limited to, cornea, skin, veins, arteries, bones, tendons and valves, such as heart valves and the like.

In one embodiment, the stem cells reduce inflammation in the organ. For example, the organ can be exposed to the stem cells for a time and dose sufficient to reduce inflammation in the organ.

In one embodiment, the stem cells reduce the occurrence of inflammatory cells in the organ. For example, the organ can be exposed to the stem cells for a time and with a dose sufficient to reduce the occurrence of inflammatory cells in the organ.

In one embodiment, the stem cells reduce inflammatory cytokines in the organ. For example, the organ can be exposed to the stem cells for a time and with a dose sufficient to reduce inflammatory cytokines in the organ.

In one embodiment, the stem cells reduce the occurrence of pulmonary edema. For example, the organ can be exposed to the stem cells for a time and with a dose sufficient to reduce the occurrence of pulmonary edema.

In one embodiment, the stem cells increase the occurrence of IL-10 expression (protein and/or mRNA) in pulmonary tissue. For example, the organ can be exposed to the stem cells for a time and with a dose sufficient to increase the occurrence of IL-10 expression in pulmonary tissue.

In one embodiment injury results from hypoxia in the organ.

In one embodiment, the stem cells reduce the effects of hypoxia in the organ.

In one embodiment, the stem cells are administered at any time between removal of the organ from the donor and transplantation into the recipient.

In one embodiment, the stem cells are exposed to the organ during the transplantation procedure.

In one embodiment, the organ can be exposed to the stem cells while the organ is still intact in the donor but before removal of the organ from the donor.

In one embodiment, the organ can be exposed to the stem cells for a period of time. The period of time can depend upon the particular organ. For example, the period of time can be about 1-2 hours, about 2-3 hours, about 3-4 hours, about 4-5 hours, about 5-6 hours, about 7-8 hours, about 8-9 hours, about 9-10 hours, or about 10 hours or more. One example of a suitable period of time is described by Zhao et al., *BMC Medicine* 2012, 10:3, which is incorporated by reference herein for the teaching of an ex vivo procedure, including suitable time periods, for an intravenous ex vivo cell process.

In one embodiment, the concentration of stem cells exposed to the organ can depend upon the particular organ. For example, the concentration of cells exposed to the organ can be about 0.01 to about $5 \times 10^7$ cells/ml, about $1 \times 10^5$ cells/ml to about $5 \times 10^7$ cells/ml, or about $10 \times 10^6$ cells/ml.

In another embodiment, the concentration of stem cells exposed to the organ can be about $1 \times 10^5$ cells/kg organ to about $5 \times 10^5$ cells/kg organ, about $5 \times 10^5$ cells/kg organ to $1 \times 10^6$ cells/kg organ to $5 \times 10^6$ cells/kg organ, about $5 \times 10^6$ cells/kg organ to $1 \times 10^7$ cells/kg organ, about $1 \times 10^7$ cells/kg organ to $1.5 \times 10^7$ cells/kg organ, or about $1 \times 10^7$ cells/kg organ to $2 \times 10^8$ cells/kg organ.

In other embodiments, the stem cells are contained in a fluid for perfusion into the organ or in a carrier for intra-organ (such as intra-bronchially) administration.

In another embodiment, the stem cells are contained in a medium in which the organ is contacted prior to transplantation, such as a medium in which the organ is bathed rather than being perfused.

The inventors contemplate using any desired stem cell in the methods of the invention. These include, but are not limited to, embryonic stem cells, non-embryonic multipotent stem cells, mesenchymal stem cells, neural stem cells, induced pluripotent stem cells, and the like. In one embodiment, the stem cells can be non-HLA matched, allogeneic cells.

Cells include, but are not limited to, cells that are not embryonic stem cells and not germ cells, having some characteristics of embryonic stem cells, but being derived from non-embryonic tissue, and providing the effects described in this application. The cells may naturally achieve these effects (i.e., not genetically or pharmaceutically modified). However, natural expressors can be genetically or pharmaceutically modified to increase potency.

The cells may express pluripotency markers, such as oct4. They may also express markers associated with extended replicative capacity, such as telomerase. Other characteristics of pluripotency can include the ability to differentiate into cell types of more than one germ layer, such as two or three of ectodermal, endodermal, and mesodermal embryonic germ layers. Such cells may or may not be immortalized or transformed in culture. The cells may be highly expanded without being transformed and also maintain a normal karyotype. In one embodiment, the non-embryonic stem, non-germ cells may have undergone a desired number of cell doublings in culture. For example, non-embryonic stem, non-germ cells may have undergone at least 10-40 cell doublings in culture, such as 30-35 cell doublings, wherein the cells are not transformed and have a normal karyotype. The cells may differentiate into at least one cell type of each of two of the endodermal, ectodermal, and mesodermal embryonic lineages and may include differentiation into all three. Further, the cells may not be tumorigenic, such as not producing teratomas. If cells are transformed or tumorigenic, and it is desirable to use them for infusion, such cells may be disabled so they cannot form tumors in vivo, as by treatment that prevents cell proliferation into tumors. Such treatments are well known in the art.

Cells include, but are not limited to, the following numbered embodiments:

1. Isolated expanded non-embryonic stem, non-germ cells, the cells having undergone at least 10-40 cell doublings in culture, wherein the cells express oct4, are not transformed, and have a normal karyotype.

2. The non-embryonic stem, non-germ cells of 1 above that further express one or more of telomerase, rex-1, rox-1, or sox-2.

3. The non-embryonic stem, non-germ cells of 1 above that can differentiate into at least one cell type of at least two of the endodermal, ectodermal, and mesodermal embryonic lineages.

4. The non-embryonic stem, non-germ cells of 3 above that further express one or more of telomerase, rex-1, rox-1, or sox-2.

5. The non-embryonic stem, non-germ cells of 3 above that can differentiate into at least one cell type of each of the endodermal, ectodermal, and mesodermal embryonic lineages.

6. The non-embryonic stem, non-germ cells of 5 above that further express one or more of telomerase, rex-1, rox-1, or sox-2.

7. Isolated expanded non-embryonic stem, non-germ cells that are obtained by culture of non-embryonic, non-germ tissue, the cells having undergone at least 40 cell doublings in culture, wherein the cells are not transformed and have a normal karyotype.

8. The non-embryonic stem, non-germ cells of 7 above that express one or more of oct4, telomerase, rex-1, rox-1, or sox-2.

9. The non-embryonic stem, non-germ cells of 7 above that can differentiate into at least one cell type of at least two of the endodermal, ectodermal, and mesodermal embryonic lineages.

10. The non-embryonic stem, non-germ cells of 9 above that express one or more of oct4, telomerase, rex-1, rox-1, or sox-2.

11. The non-embryonic stem, non-germ cells of 9 above that can differentiate into at least one cell type of each of the endodermal, ectodermal, and mesodermal embryonic lineages.

12. The non-embryonic stem, non-germ cells of 11 above that express one or more of oct4, telomerase, rex-1, rox-1, or sox-2.

13. Isolated expanded non-embryonic stem, non-germ cells, the cells having undergone at least 10-40 cell doublings in culture, wherein the cells express telomerase, are not transformed, and have a normal karyotype.

14. The non-embryonic stem, non-germ cells of 13 above that further express one or more of oct4, rex-1, rox-1, or sox-2.

15. The non-embryonic stem, non-germ cells of 13 above that can differentiate into at least one cell type of at least two of the endodermal, ectodermal, and mesodermal embryonic lineages.

16. The non-embryonic stem, non-germ cells of 15 above that further express one or more of oct4, rex-1, rox-1, or sox-2.

17. The non-embryonic stem, non-germ cells of 15 above that can differentiate into at least one cell type of each of the endodermal, ectodermal, and mesodermal embryonic lineages.

18. The non-embryonic stem, non-germ cells of 17 above that further express one or more of oct4, rex-1, rox-1, or sox-2.

19. Isolated expanded non-embryonic stem, non-germ cells that can differentiate into at least one cell type of at least two of the endodermal, ectodermal, and mesodermal embryonic lineages, said cells having undergone at least 10-40 cell doublings in culture.

20. The non-embryonic stem, non-germ cells of 19 above that express one or more of oct4, telomerase, rex-1, rox-1, or sox-2.

21. The non-embryonic stem, non-germ cells of 19 above that can differentiate into at least one cell type of each of the endodermal, ectodermal, and mesodermal embryonic lineages.

22. The non-embryonic stem, non-germ cells of 21 above that express one or more of oct4, telomerase, rex-1, rox-1, or sox-2.

In one embodiment, a conditioned medium is used instead of the stem cells.

In one embodiment, the organ is from a human.

In view of the property of the cells to achieve the desired effects, cell banks can be established containing cells that are selected for having a desired potency (level of ability) to achieve the effects. Accordingly, the invention encompasses assaying cells for the ability. The bank can provide a source for making a pharmaceutical composition to administer to an organ. Cells can be used directly from the bank or expanded prior to use. Especially in the case that the cells are subjected to further expansion, after expansion it is desirable to validate that the cells still have the desired potency. Banks allow the "off the shelf" use of cells that are allogeneic to the organ donor and recipient.

Accordingly, the invention also is directed to diagnostic procedures conducted prior to exposing the stem cells to an organ. The procedures include assessing the potency of the cells to achieve the effects described in this application. The cells may be taken from a cell bank and used directly or expanded prior to administration. In either case, the cells could be assessed for the desired potency. Especially in the case that the cells are subjected to further expansion, after expansion it is desirable to validate that the cells still have the desired potency.

Although the cells selected for the effects are necessarily assayed during the selection procedure, it may be preferable, and prudent, to again assay the cells prior to administration to a subject for treatment to confirm that the cells still achieve the effects at desired levels. This is particularly preferable where the cells have been stored for any length of time, such as in a cell bank, where cells are, most likely, frozen during storage.

Between the original isolation of the cells and the administration to an organ, there may be multiple (i.e., sequential) assays for the effects. This is to confirm that the cells can still achieve the effects, at desired levels, after manipulations that occur within this time frame. For example, an assay may be performed after each expansion of the cells. If cells are stored in a cell bank, they may be assayed after being released from storage. If they are frozen, they may be assayed after thawing. If the cells from a cell bank are expanded, they may be assayed after expansion. Preferably, a portion of the final cell product (that is physically administered to the organ) may be assayed.

Since the stem cells may provide the effects described herein by means of secreted molecules, the various embodiments described herein for administration of stem cells may be done by administration of one or more of the secreted molecules, such as might be in conditioned culture medium.

The invention is also directed to compositions comprising a population of the cells having a desired potency to achieve the desired effects. Such populations may be found as pharmaceutical compositions suitable for administration to an organ and/or in cell banks from which cells can be used directly for administration or expanded prior to administration. In one embodiment, the cells have enhanced (increased) potency compared to the previous (parent) cell population. Parent cells are as defined herein. Enhancement can be by selection of natural expressors or by external factors acting on the cells.

The cells may be prepared by the isolation and culture conditions described herein. In a specific embodiment, they are prepared by culture conditions that are described herein involving lower oxygen concentrations combined with higher serum, such as those used to prepare the cells designated "MultiStem®."

DETAILED DESCRIPTION OF THE INVENTION

Figure 1:
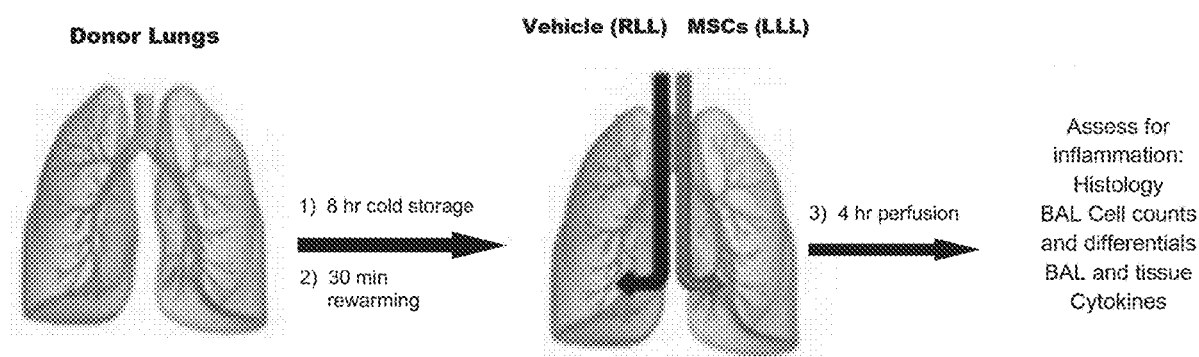
FIG. 1. Schematic of study design.

It should be understood that this invention is not limited to the particular methodology, protocols, and reagents, etc., described herein and, as such, may vary. The terminology used herein is for the purpose of describing particular embodiments only, and is not intended to limit the scope of the disclosed invention, which is defined solely by the claims.

The section headings are used herein for organizational purposes only and are not to be construed as in any way limiting the subject matter described.

The methods and techniques of the present application are generally performed according to conventional methods well-known in the art and as described in various general and more specific references that are cited and discussed throughout the present specification unless otherwise indicated. See, e.g., Sambrook et al., *Molecular Cloning: A Laboratory Manual*, 3rd ed., Cold Spring Harbor Laboratory Press, Cold Spring Harbor, N.Y. (2001) and Ausubel et al., *Current Protocols in Molecular Biology*, Greene Publishing Associates (1992), and Harlow and Lane, *Antibodies: A Laboratory Manual*, Cold Spring Harbor Laboratory Press, Cold Spring Harbor, N.Y. (1990).

Definitions

"A" or "an" means herein one or more than one; at least one. Where the plural form is used herein, it generally includes the singular.

A "cell bank" is industry nomenclature for cells that have been grown and stored for future use. Cells may be stored in aliquots. They can be used directly out of storage or may be expanded after storage. This is a convenience so that there are "off the shelf" cells available for administration. The cells may already be stored in a pharmaceutically-acceptable excipient so they may be directly administered or they may be mixed with an appropriate excipient when they are released from storage. Cells may be frozen or otherwise stored in a form to preserve viability. In one embodiment of the invention, cell banks are created in which the cells have been selected for enhanced potency to achieve the effects described in this application. Following release from storage, and prior to administration, it may be preferable to again assay the cells for potency. This can be done using any of the assays, direct or indirect, described in this application or otherwise known in the art. Then cells having the desired potency can then be administered. Banks can be made using autologous cells (derived from the organ donor or recipient). Or banks can contain cells for allogeneic uses.

"Co-administer" means to administer in conjunction with one another, together, coordinately, including simultaneous or sequential administration of two or more agents.

"Comprising" means, without other limitation, including the referent, necessarily, without any qualification or exclusion on what else may be included. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them. "Comprised of" and similar phrases using words of the root "comprise" are used herein as synonyms of "comprising" and have the same meaning.

"Comprised of" is a synonym of "comprising" (see above).

The term "contact", when used in relation to a stem cell and an organ to be transplanted, can mean that, upon exposure to the organ, the stem cell physically touches the organ. In such instances, the stem cell is in direct contact with the organ. In other instances, the stem cell can indirectly contact the organ where one or more structures (e.g., another cell) and/or fluids (e.g., blood) physically intervene(s) between the stem cell and the organ.

"EC cells" were discovered from analysis of a type of cancer called a teratocarcinoma. In 1964, researchers noted that a single cell in teratocarcinomas could be isolated and remain undifferentiated in culture. This type of stem cell became known as an embryonic carcinoma cell (EC cell).

"Effective amount" generally means an amount which provides the desired local or systemic effect, e.g., effective to ameliorate undesirable effects of inflammation, including achieving the specific desired effects described in this application. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each organ, including the type of organ, disease or injury being treated, the way the organ has been processed, length of time from collection, etc. One skilled in the art will be able to determine the effective amount for a given organ based on these considerations which are routine in the art. As used herein, "effective dose" means the same as "effective amount."

"Effective route" generally means a route which provides for delivery of an agent to a desired compartment, system, or location. For example, an effective route is one through which an agent can be administered to provide at the desired site of action an amount of the agent sufficient to effectuate a beneficial or desired clinical result (in the present case, effective transplantation).

"Embryonic Stem Cells (ESC)" are well known in the art and have been prepared from many different mammalian species. Embryonic stem cells are stem cells derived from the inner cell mass of an early stage embryo known as a blastocyst. They are able to differentiate into all derivatives of the three primary germ layers: ectoderm, endoderm, and mesoderm. These include each of the more than 220 cell types in the adult body. The ES cells can become any tissue in the body, excluding placenta. Only the morula's cells are totipotent, able to become all tissues and a placenta. Some cells similar to ESCs may be produced by nuclear transfer of a somatic cell nucleus into an enucleated fertilized egg.

The term "exogenous", when used in relation to a stem cell, generally refers to a stem cell that is external to the organ and which has been exposed to (e.g., contacted with) an organ intended for transplantation by an effective route. An exogenous stem cell may be from the same subject or from a different subject. In one embodiment, exogenous stem cells can include stem cells that have been harvested from a subject, isolated, expanded ex vivo, and then exposed to an organ intended for transplantation by an effective route.

The term "expose" can include the act of administering one or more stem cells to an organ intended for transplantation. Administration to the organ can be done ex vivo or in vivo (e.g., by perfusion into a subject).

Use of the term "includes" is not intended to be limiting.

"Increase" or "increasing" means to induce a biological event entirely or to increase the degree of the event.

"Induced pluripotent stem cells (IPSC or IPS cells)" are somatic cells that have been reprogrammed, for example, by introducing exogenous genes that confer on the somatic cell a less differentiated phenotype. These cells can then be induced to differentiate into less differentiated progeny. IPS cells have been derived using modifications of an approach originally discovered in 2006 (Yamanaka, S. et al., *Cell Stem Cell*, 1:39-49 (2007)). For example, in one instance, to create IPS cells, scientists started with skin cells that were then modified by a standard laboratory technique using retroviruses to insert genes into the cellular DNA. In one instance, the inserted genes were Oct4, Sox2, Lif4, and c-myc, known to act together as natural regulators to keep cells in an embryonic stem cell-like state. These cells have been described in the literature. See, for example, Wernig et al., *PNAS*, 105:5856-5861 (2008); Jaenisch et al., *Cell*, 132:567-582 (2008); Hanna et al., *Cell*, 133:250-264 (2008); and Brambrink et al., *Cell Stem Cell*, 2:151-159 (2008). These references are incorporated by reference for teaching IPSCs and methods for producing them. It is also possible that such cells can be created by specific culture conditions (exposure to specific agents).

The term "ischemic reperfusion injury" is understood in the industry and is described for example in http://emedicine.medscape.com/article/431140-overview#aw2aab6b3 (about Organ Preservation), as well as Groot, H. et al., *Transplant Proc.* 39(2):481-4 (March 2007), which are incorporated herein by reference for the teaching of ischemic reperfusion injury and its mechanistic details.

"Ischemia" occurs in two phases. The first phase is referred to as the warm ischemic phase and includes the time from which the donor organ is removed and circulation is interrupted to the time that the organ is administered with a hypothermic preservation solution. The cold ischemic phase occurs when the organ is preserved in a hypothermic state prior to transplantation and normal recirculation in the recipient.

The term "isolated" refers to a cell or cells which are not associated with one or more cells or one or more cellular components that are associated with the cell or cells in vivo. An "enriched population" means a relative increase in numbers of a desired cell relative to one or more other cell types in vivo or in primary culture.

However, as used herein, the term "isolated" does not indicate the presence of only the cells of the invention. Rather, the term "isolated" indicates that the cells of the invention are removed from their natural tissue environment and are present at a higher concentration as compared to the normal tissue environment. Accordingly, an "isolated" cell population may further include cell types in addition to the cells of the invention cells and may include additional tissue components. This also can be expressed in terms of cell doublings, for example. A cell may have undergone 10, 20, 30, 40 or more doublings in vitro or ex vivo so that it is enriched compared to its original numbers in vivo or in its original tissue environment (e.g., bone marrow, peripheral blood, placenta, umbilical cord, umbilical cord blood, adipose tissue, etc.).

"MAPC" is an acronym for "multipotent adult progenitor cell." It refers to a cell that is not an embryonic stem cell or germ cell but has some characteristics of these. MAPC can be characterized in a number of alternative descriptions, each of which conferred novelty to the cells when they were discovered. They can, therefore, be characterized by one or more of those descriptions. First, they have extended replicative capacity in culture without being transformed (tumorigenic) and with a normal karyotype. Second, they may give rise to cell progeny of more than one germ layer, such as two or all three germ layers (i.e., endoderm, mesoderm and ectoderm) upon differentiation. Third, although they are not embryonic stem cells or germ cells, they may express markers of these primitive cell types so that MAPCs may express one or more of Oct 3/4 (i.e., Oct 3A), rex-1, and rox-1. They may also express one or more of sox-2 and SSEA-4. Fourth, like a stem cell, they may self-renew, that is, have an extended replication capacity without being transformed. This means that these cells express telomerase (i.e., have telomerase activity). Accordingly, the cell type that was designated "MAPC" may be characterized by alternative basic characteristics that describe the cell via some of its novel properties.

The term "adult" in MAPC is non-restrictive. It refers to a non-embryonic somatic cell. MAPCs are karyotypically normal and do not form teratomas in vivo. This acronym was first used in U.S. Pat. No. 7,015,037 to describe a pluripotent cell isolated from bone marrow. However, cells with pluripotential markers and/or differentiation potential have been discovered subsequently and, for purposes of this invention, may be equivalent to those cells first designated "MAPC." Essential descriptions of the MAPC type of cell are provided in the Summary of the Invention above.

MAPC represents a more primitive progenitor cell population than MSC (Verfaillie, C. M., *Trends Cell Biol* 12:502-8 (2002), Jahagirdar, B. N., et al., *Exp Hematol*, 29:543-56 (2001); Reyes, M. and C. M. Verfaillie, *Ann N Y*

*Acad Sci*, 938:231-233 (2001); Jiang, Y. et al., *Exp Hematol*, 30896-904 (2002); and Jiang, Y. et al., *Nature*, 418:41-9. (2002)).

The term "MultiStem®" is the trade name for a cell preparation based on the MAPCs of U.S. Pat. No. 7,015,037, i.e., a non-embryonic stem, non-germ cell as described above. MultiStem® is prepared according to cell culture methods disclosed in this patent application, particularly, lower oxygen and higher serum. MultiStem® is highly expandable, karyotypically normal, and does not form teratomas in vivo. It may differentiate into cell lineages of more than one germ layer and may express one or more of telomerase, oct3/4, rex-1, rox-1, sox-2, and SSEA4.

The term "organ" may be used according to its customary and understood meaning in the industry as an entire intact organ that has been removed from the donor for transplantation or is intended to be removed from the donor for transplantation into a recipient. Although the term "organ" is emphasized in this application, the methods apply to tissues that may not constitute whole organs. That is, to parts of organs such as those disclosed elsewhere in this application. Therefore, where appropriate, the term "tissue" can be appropriately substituted for the term "organ".

"Pharmaceutically-acceptable carrier" is any pharmaceutically-acceptable medium for the cells used in the present invention. Such a medium may retain isotonicity, cell metabolism, pH, and the like. It is compatible with administration to an organ and can be used, therefore, for cell delivery and treatment.

The term "potency" refers to the ability of the cells to achieve the effects described in this application. Accordingly, potency refers to the effect at various levels, including, but not limited to, increasing the probability of a successful transplantation, retarding the deterioration of a pre-transplant organ, reducing inflammatory activity in the organ, providing immunological tolerance to the organ, increasing the production of anti-inflammatory cytokines in the organ, increasing the presence of neuroprotective T-cells in the organ, decreasing the presence of reactive T-cells in the organ, reducing the level of pro-inflammatory cytokines in the organ, reducing the effects of hypoxia in the organ, reversing the level of edema in the organ, and reducing the effects of hypothermia in the organ. Injury that is sustained during recovery, preservation, and transplantation, occurs mainly from ischemia and hypothermia. These can affect the organs in various ways. These are described in the Medscape reference cited above and the link is given in this application. According to that reference, the mechanisms of tissue injury include a loss of integrity in the cell structure, disruption of the ionic composition of the cell, disruption in ATP generation, and, as a result of reperfusion, damage may occur during reperfusion by the toxic accumulation of oxygen free radicals.

With respect to integrity of the cell structure, integrity may be interrupted by loss of structural integrity in the cell membrane. Maintaining the integrity of the cell membrane depends on control of temperature, pH, osmolarity. Organ ischemia and preservation disrupt all of these parameters.

"Primordial embryonic germ cells" (PG or EG cells) can be cultured and stimulated to produce many less differentiated cell types.

"Progenitor cells" are cells produced during differentiation of a stem cell that have some, but not all, of the characteristics of their terminally-differentiated progeny. Defined progenitor cells, such as "cardiac progenitor cells," are committed to a lineage, but not to a specific or terminally differentiated cell type. The term "progenitor" as used in the acronym "MAPC" does not limit these cells to a particular lineage. A progenitor cell can form a progeny cell that is more highly differentiated than the progenitor cell.

The term "reduce" as used herein means to prevent as well as decrease. In the context of organ treatment, to "reduce" is to either prevent or ameliorate organ rejection. This includes causes or symptoms of organ rejection. This applies, for example, to the underlying biological cause of rejection, such as, ameliorating the deleterious effects of inflammation.

"Selecting" a cell with a desired level of potency can mean identifying (as by assay), isolating, and expanding a cell. This could create a population that has a higher potency than the parent cell population from which the cell was isolated. The "parent" cell population refers to the parent cells from which the selected cells divided. "Parent" refers to an actual P1→F1 relationship (i.e., a progeny cell). So if cell X is isolated from a mixed population of cells X and Y, in which X is an expressor and Y is not, one would not classify a mere isolate of X as having enhanced expression. But, if a progeny cell of X is a higher expressor, one would classify the progeny cell as having enhanced expression.

To select a cell that achieves the desired effect would include both an assay to determine if the cells achieve the desired effect and would also include obtaining those cells. The cell may naturally achieve the desired effect in that the effect is not achieved by an exogenous transgene/DNA. But an effective cell may be improved by being incubated with or exposed to an agent that increases the effect. The cell population from which the effective cell is selected may not be known to have the potency prior to conducting the assay. The cell may not be known to achieve the desired effect prior to conducting the assay. As an effect could depend on gene expression and/or secretion, one could also select on the basis of one or more of the genes that cause the effect.

Selection could be from cells in a tissue. For example, in this case, cells would be isolated from a desired tissue, expanded in culture, selected for achieving the desired effect, and the selected cells further expanded.

Selection could also be from cells ex vivo, such as cells in culture. In this case, one or more of the cells in culture would be assayed for achieving the desired effect and the cells obtained that achieve the desired effect could be further expanded.

Cells could also be selected for enhanced ability to achieve the desired effect. In this case, the cell population from which the enhanced cell is obtained already has the desired effect. Enhanced effect means a higher average amount per cell than in the parent population.

The parent population from which the enhanced cell is selected may be substantially homogeneous (the same cell type). One way to obtain such an enhanced cell from this population is to create single cells or cell pools and assay those cells or cell pools to obtain clones that naturally have the enhanced (greater) effect (as opposed to treating the cells with a modulator that induces or increases the effect) and then expanding those cells that are naturally enhanced.

However, cells may be treated with one or more agents that will induce or increase the effect. Thus, substantially homogeneous populations may be treated to enhance the effect.

If the population is not substantially homogeneous, then, it is preferable that the parental cell population to be treated contains at least 100 of the desired cell type in which enhanced effect is sought, more preferably at least 1,000 of the cells, and still more preferably, at least 10,000 of the cells. Following treatment, this sub-population can be recovered from the heterogeneous population by known cell selection techniques and further expanded if desired.

Thus, desired levels of effect may be those that are higher than the levels in a given preceding population. For example, cells that are put into primary culture from a tissue and expanded and isolated by culture conditions that are not specifically designed to produce the effect may provide a parent population. Such a parent population can be treated to enhance the average effect per cell or screened for a cell or cells within the population that express greater degrees of effect without deliberate treatment. Such cells can be expanded then to provide a population with a higher (desired) expression.

"Self-renewal" of a stem cell refers to the ability to produce replicate daughter stem cells having differentiation potential that is identical to those from which they arose. A similar term used in this context is "proliferation."

"Stem cell" means a cell that can undergo self-renewal (i.e., progeny with the same differentiation potential) and also produce progeny cells that are more restricted in differentiation potential. Within the context of the invention, a stem cell would also encompass a more differentiated cell that has de-differentiated, for example, by nuclear transfer, by fusion with a more primitive stem cell, by introduction of specific transcription factors, or by culture under specific conditions. See, for example, Wilmut et al., Nature, 385:810-813 (1997); Ying et al., Nature, 416:545-548 (2002); Guan et al., Nature, 440:1199-1203 (2006); Takahashi et al., Cell, 126:663-676 (2006); Okita et al., Nature, 448:313-317 (2007); and Takahashi et al., Cell, 131:861-872 (2007).

Dedifferentiation may also be caused by the administration of certain compounds or exposure to a physical environment in vitro or in vivo that would cause the dedifferentiation. Stem cells also may be derived from abnormal tissue, such as a teratocarcinoma and some other sources such as embryoid bodies (although these can be considered embryonic stem cells in that they are derived from embryonic tissue, although not directly from the inner cell mass). Stem cells may also be produced by introducing genes associated with stem cell function into a non-stem cell, such as an induced pluripotent stem cell.

"Subject" means a vertebrate, such as a mammal, such as a human. Mammals include, but are not limited to, humans, dogs, cats, horses, cows, and pigs.

The term "therapeutically effective amount" refers to the amount of an agent determined to produce any therapeutic response in a mammal. For example, effective anti-inflammatory therapeutic agents may prolong the survivability of the patient, and/or inhibit overt clinical symptoms. Treatments that are therapeutically effective within the meaning of the term as used herein, include treatments that improve a subject's quality of life even if they do not improve the disease outcome per se. Such therapeutically effective amounts are readily ascertained by one of ordinary skill in the art. Thus, to "treat" means to deliver such an amount. Thus, treating can prevent or ameliorate any pathological symptoms.

The term "tolerization" or "tolerize" refers to the treatment of the pre-transplantation organ (graft) with the stem cells to reduce the immunogenicity of the graft to enable or facilitate the development of tolerance of the organ by the recipient. The term broadly refers to the concept of reducing the immunogenicity of the transplant organ, which enables or facilitates tolerance development by the recipient. Thus, tolerizing the organ causes the organ to be tolerated by the recipient. In other words, the term can refer to making the immune system unable to elicit an immune response to a cell or tissue that normally elicits an immune response. An example of this is when a T-regulatory cell secretes factors that suppress an activated T-cell so that I can no longer secreted pro-inflammatory cytokines.

This might be accomplished via ex vivo treatment prior to transplantation, or even local administration prior to harvest.

"Treat," "treating," or "treatment" are used broadly in relation to the invention and each such term encompasses, among others, preventing, ameliorating, inhibiting, or curing a deficiency, dysfunction, disease, or other deleterious process, including those that interfere with and/or result from a therapy.

"Validate" means to confirm. In the context of the invention, one confirms that a cell is an expressor with a desired potency. This is so that one can then use that cell (in treatment, banking, drug screening, etc.) with a reasonable expectation of efficacy. Accordingly, to validate means to confirm that the cells, having been originally found to have/established as having the desired activity, in fact, retain that activity. Thus, validation is a verification event in a two-event process involving the original determination and the follow-up determination. The second event is referred to herein as "validation."

Stem Cells

The present invention can be practiced, preferably, using stem cells of vertebrate species, such as humans, non-human primates, domestic animals, livestock, and other non-human mammals. These include, but are not limited to, those cells described below.

Embryonic Stem Cells

The most well studied stem cell is the embryonic stem cell (ESC) as it has unlimited self-renewal and multipotent differentiation potential. These cells are derived from the inner cell mass of the blastocyst or can be derived from the primordial germ cells of a post-implantation embryo (embryonal germ cells or EG cells). ES and EG cells have been derived, first from mouse, and later, from many different animals, and more recently, also from non-human primates and humans. When introduced into mouse blastocysts or blastocysts of other animals, ESCs can contribute to all tissues of the animal. ES and EG cells can be identified by positive staining with antibodies against SSEA1 (mouse) and SSEA4 (human) See, for example, U.S. Pat. Nos. 5,453,357; 5,656,479; 5,670,372; 5,843,780; 5,874,301; 5,914,268; 6,110,739 6,190,910; 6,200,806; 6,432,711; 6,436,701, 6,500,668; 6,703,279; 6,875,607; 7,029,913; 7,112,437; 7,145,057; 7,153,684; and 7,294,508, each of which is incorporated by reference for teaching embryonic stem cells and methods of making and expanding them. Accordingly, ESCs and methods for isolating and expanding them are well-known in the art.

A number of transcription factors and exogenous cytokines have been identified that influence the potency status of embryonic stem cells in vivo. The first transcription factor to be described that is involved in stem cell pluripotency is Oct4. Oct4 belongs to the POU (Pit-Oct-Unc) family of transcription factors and is a DNA binding protein that is able to activate the transcription of genes, containing an octameric sequence called "the octamer motif" within the promoter or enhancer region. Oct4 is expressed at the moment of the cleavage stage of the fertilized zygote until the egg cylinder is formed. The function of Oct3/4 is to repress differentiation inducing genes (i.e., FoxaD3, hCG) and to activate genes promoting pluripotency (FGF4, Utf1, Rex1). Sox2, a member of the high mobility group (HMG) box transcription factors, cooperates with Oct4 to activate transcription of genes expressed in the inner cell mass. It is essential that Oct3/4 expression in embryonic stem cells is maintained between certain levels. Overexpression or downregulation of >50% of Oct4 expression level will alter embryonic stem cell fate, with the formation of primitive endoderm/mesoderm or trophectoderm, respectively. In vivo, Oct4 deficient embryos develop to the blastocyst stage, but the inner cell mass cells are not pluripotent. Instead they differentiate along the extraembryonic trophoblast lineage. Sall4, a mammalian Spalt transcription factor, is an upstream regulator of Oct4, and is therefore important to maintain appropriate levels of Oct4 during early phases of embryology. When Sall4 levels fall below a certain threshold, trophectodermal cells will expand ectopically into the inner cell mass. Another transcription factor required for pluripotency is Nanog, named after a celtic tribe "Tir Nan Og": the land of the ever young. In vivo, Nanog is expressed from the stage of the compacted morula, is subsequently defined to the inner cell mass and is downregulated by the implantation stage. Downregulation of Nanog may be important to avoid an uncontrolled expansion of pluripotent cells and to allow multilineage differentiation during gastrulation. Nanog null embryos, isolated at day 5.5, consist of a disorganized blastocyst, mainly containing extraembryonic endoderm and no discernible epiblast.

Non-Embryonic Stem Cells

Stem cells have been identified in most tissues. Perhaps the best characterized is the hematopoietic stem cell (HSC). HSCs are mesoderm-derived cells that can be purified using cell surface markers and functional characteristics. They have been isolated from bone marrow, peripheral blood, cord blood, fetal liver, and yolk sac. They initiate hematopoiesis and generate multiple hematopoietic lineages. When transplanted into lethally-irradiated animals, they can repopulate the erythroid neutrophil-macrophage, megakaryocyte, and lymphoid hematopoietic cell pool. They can also be induced to undergo some self-renewal cell division. See, for example, U.S. Pat. Nos. 5,635,387; 5,460,964; 5,677,136; 5,750,397; 5,681,599; and 5,716,827. U.S. Pat. No. 5,192,553 reports methods for isolating human neonatal or fetal hematopoietic stem or progenitor cells. U.S. Pat. No. 5,716,827 reports human hematopoietic cells that are Thy-1+ progenitors, and appropriate growth media to regenerate them in vitro. U.S. Pat. No. 5,635,387 reports a method and device for culturing human hematopoietic cells and their precursors. U.S. Pat. No. 6,015,554 describes a method of reconstituting human lymphoid and dendritic cells. Accordingly, HSCs and methods for isolating and expanding them are well-known in the art.

Another stem cell that is well-known in the art is the neural stem cell (NSC). These cells can proliferate in vivo and continuously regenerate at least some neuronal cells. When cultured ex vivo, neural stem cells can be induced to proliferate as well as differentiate into different types of neurons and glial cells. When transplanted into the brain, neural stem cells can engraft and generate neural and glial cells. See, for example, Gage F. H., Science, 287:1433-1438 (2000), Svendsen S. N. et al., Brain Pathology, 9:499-513 (1999), and Okabe S. et al., Mech Development, 59:89-102 (1996). U.S. Pat. No. 5,851,832 reports multipotent neural stem cells obtained from brain tissue. U.S. Pat. No. 5,766,948 reports producing neuroblasts from newborn cerebral hemispheres. U.S. Pat. Nos. 5,564,183 and 5,849,553 report the use of mammalian neural crest stem cells. U.S. Pat. No. 6,040,180 reports in vitro generation of differentiated neurons from cultures of mammalian multipotential CNS stem cells. WO 98/50526 and WO 99/01159 report generation and isolation of neuroepithelial stem cells, oligodendrocyte-astrocyte precursors, and lineage-restricted neuronal precursors. U.S. Pat. No. 5,968,829 reports neural stem cells obtained from embryonic forebrain. Accordingly, neural stem cells and methods for making and expanding them are well-known in the art.

Another stem cell that has been studied extensively in the art is the mesenchymal stem cell (MSC). MSCs are derived from the embryonal mesoderm and can be isolated from many sources, including adult bone marrow, peripheral blood, fat, placenta, and umbilical blood, among others. MSCs can differentiate into many mesodermal tissues, including muscle, bone, cartilage, fat, and tendon. There is considerable literature on these cells. See, for example, U.S. Pat. Nos. 5,486,389; 5,827,735; 5,811,094; 5,736,396; 5,837,539; 5,837,670; and 5,827,740. See also Pittenger, M. et al., Science, 284:143-147 (1999).

Another example of an adult stem cell is adipose-derived adult stem cells (ADSCs) which have been isolated from fat, typically by liposuction followed by release of the ADSCs using collagenase. ADSCs are similar in many ways to MSCs derived from bone marrow, except that it is possible to isolate many more cells from fat. These cells have been reported to differentiate into bone, fat, muscle, cartilage, and neurons. A method of isolation has been described in U.S. Patent Publication No. 2005/0153442 A1.

Other stem cells that are known in the art include gastrointestinal stem cells, epidermal stem cells, and hepatic stem cells, which have also been termed "oval cells" (Potten, C., et al., Trans R Soc Lond B Biol Sci, 353:821-830 (1998), Watt, F., Trans R Soc Lond B Biol Sci, 353:831 (1997); Alison et al., Hepatology, 29:678-683 (1998).

Other non-embryonic cells reported to be capable of differentiating into cell types of more than one embryonic germ layer include, but are not limited to, cells from umbilical cord blood (see U.S. Publication No. 2002/0164794), placenta (see U.S. Publication No. 2003/0181269, umbilical cord matrix (Mitchell, K. E. et al., Stem Cells, 21:50-60 (2003)), small embryonic-like stem cells (Kucia, M. et al., J Physiol Pharmacol, 57 Suppl 5:5-18 (2006)), amniotic fluid stem cells (Atala, A., J Tissue Regen Med, 1:83-96 (2007)), skin-derived precursors (Toma et al., Nat Cell Biol, 3:778-784 (2001)), bone marrow (see U.S. Patent Publication Nos. 2003/0059414 and 2006/0147246), marrow-isolated adult multilineage inducible (MIAMI) cells (see PCT/US2004/002580), and endometrial cells (see U.S. Publication No. 2013/0156726), each of which is incorporated by reference for teaching these cells.

Strategies of Reprogramming Somatic Cells

Several different strategies, such as nuclear transplantation, cellular fusion, and culture induced reprogramming have been employed to induce the conversion of differentiated cells into an embryonic state. Nuclear transfer involves the injection of a somatic nucleus into an enucleated oocyte, which, upon transfer into a surrogate mother, can give rise to a clone ("reproductive cloning"), or, upon explantation in culture, can give rise to genetically matched embryonic stem (ES) cells ("somatic cell nuclear transfer," SCNT). Cell fusion of somatic cells with ES cells results in the generation of hybrids that show all features of pluripotent ES cells. Explantation of somatic cells in culture selects for immortal cell lines that may be pluripotent or multipotent. At present, spermatogonial stem cells are the only source of pluripotent cells that can be derived from postnatal animals. Transduction of somatic cells with defined factors can initiate reprogramming to a pluripotent state. These experimental approaches have been extensively reviewed (Hochedlinger and Jaenisch, *Nature*, 441:1061-1067 (2006) and Yamanaka, S., *Cell Stem Cell*, 1:39-49 (2007)).

Nuclear Transfer

Nuclear transplantation (NT), also referred to as somatic cell nuclear transfer (SCNT), denotes the introduction of a nucleus from a donor somatic cell into an enucleated ogocyte to generate a cloned animal such as Dolly the sheep (Wilmut et al., *Nature*, 385:810-813 (1997). The generation of live animals by NT demonstrated that the epigenetic state of somatic cells, including that of terminally differentiated cells, while stable, is not irreversible fixed but can be reprogrammed to an embryonic state that is capable of directing development of a new organism. In addition to providing an exciting experimental approach for elucidating the basic epigenetic mechanisms involved in embryonic development and disease, nuclear cloning technology is of potential interest for patient-specific transplantation medicine.

Fusion of Somatic Cells and Embryonic Stem Cells

Epigenetic reprogramming of somatic nuclei to an undifferentiated state has been demonstrated in murine hybrids produced by fusion of embryonic cells with somatic cells. Hybrids between various somatic cells and embryonic carcinoma cells (Solter, D., *Nat Rev Genet*, 7:319-327 (2006), embryonic germ (EG), or ES cells (Zwaka and Thomson, *Development*, 132:227-233 (2005)) share many features with the parental embryonic cells, indicating that the pluripotent phenotype is dominant in such fusion products. As with mouse (Tada et al., *Curr Biol*, 11:1553-1558 (2001)), human ES cells have the potential to reprogram somatic nuclei after fusion (Cowan et al., *Science*, 309: 1369-1373(2005)); Yu et al., *Science*, 318:1917-1920 (2006)). Activation of silent pluripotency markers such as Oct4 or reactivation of the inactive somatic X chromosome provided molecular evidence for reprogramming of the somatic genome in the hybrid cells. It has been suggested that DNA replication is essential for the activation of pluripotency markers, which is first observed 2 days after fusion (Do and Scholer, *Stem Cells*, 22:941-949 (2004)), and that forced overexpression of Nanog in ES cells promotes pluripotency when fused with neural stem cells (Silva et al., *Nature*, 441:997-1001 (2006)).

Culture-Induced Reprogramming

Pluripotent cells have been derived from embryonic sources such as blastomeres and the inner cell mass (ICM) of the blastocyst (ES cells), the epiblast (EpiSC cells), primordial germ cells (EG cells), and postnatal spermatogonial stem cells ("maGSCsm" "ES-like" cells). The following pluripotent cells, along with their donor cell/tissue is as follows: parthogenetic ES cells are derived from murine oocytes (Narasimha et al., *Curr Biol*, 7:881-884 (1997)); embryonic stem cells have been derived from blastomeres (Wakayama et al., *Stem Cells*, 25:986-993 (2007)); inner cell mass cells (source not applicable) (Eggan et al., *Nature*, 428:44-49 (2004)); embryonic germ and embryonal carcinoma cells have been derived from primordial germ cells (Matsui et al., *Cell*, 70:841-847 (1992)); GMCS, maSSC, and MASC have been derived from spermatogonial stem cells (Guan et al., *Nature*, 440:1199-1203 (2006); Kanatsu-Shinohara et al., *Cell*, 119:1001-1012 (2004); and Seandel et al., *Nature*, 449:346-350 (2007)); EpiSC cells are derived from epiblasts (Brons et al., *Nature*, 448:191-195 (2007); Tesar et al., *Nature*, 448:196-199(2007)); parthogenetic ES cells have been derived from human oocytes (Cibelli et al., *Science*, 295L819 (2002); Revazova et al., *Cloning Stem Cells*, 9:432-449 (2007)); human ES cells have been derived from human blastocysts (Thomson et al., *Science*, 282:1145-1147 (1998)); MAPC have been derived from bone marrow (Jiang et al., *Nature*, 418:41-49 (2002); Phinney and Prockop, *Stem Cells*, 25:2896-2902 (2007)); cord blood cells (derived from cord blood) (van de Ven et al., *Exp Hematol*, 35:1753-1765 (2007)); neurosphere derived cells derived from neural cell (Clarke et al., *Science*, 288:1660-1663 (2000)). Donor cells from the germ cell lineage such as PGCs or spermatogonial stem cells are known to be unipotent in vivo, but it has been shown that pluripotent ES-like cells (Kanatsu-Shinohara et al., *Cell*, 119:1001-1012 (2004) or maGSCs (Guan et al., *Nature*, 440:1199-1203 (2006), can be isolated after prolonged in vitro culture. While most of these pluripotent cell types were capable of in vitro differentiation and teratoma formation, only ES, EG, EC, and the spermatogonial stem cell-derived maGCSs or ES-like cells were pluripotent by more stringent criteria, as they were able to form postnatal chimeras and contribute to the germline Recently, multipotent adult spermatogonial stem cells (MASCs) were derived from testicular spermatogonial stem cells of adult mice, and these cells had an expression profile different from that of ES cells (Seandel et al., *Nature*, 449:346-350 (2007)) but similar to EpiSC cells, which were derived from the epiblast of postimplantation mouse embryos (Brons et al., *Nature*, 448:191-195 (2007); Tesar et al., *Nature*, 448:196-199 (2007)).

Reprogramming by Defined Transcription Factors

Takahashi and Yamanaka have reported reprogramming somatic cells back to an ES-like state (Takahashi and Yamanaka, *Cell*, 126:663-676 (2006)). They successfully reprogrammed mouse embryonic fibroblasts (MEFs) and adult fibroblasts to pluripotent ES-like cells after viral-mediated transduction of the four transcription factors Oct4, Sox2, c-myc, and Klf4 followed by selection for activation of the Oct4 target gene Fbx15. Cells that had activated Fbx15 were coined iPS (induced pluripotent stem) cells and were shown to be pluripotent by their ability to form teratomas, although they were unable to generate live chimeras. This pluripotent state was dependent on the continuous viral expression of the transduced Oct4 and Sox2 genes, whereas the endogenous Oct4 and Nanog genes were either not expressed or were expressed at a lower level than in ES cells, and their respective promoters were found to be largely methylated. This is consistent with the conclusion that the Fbx15-iPS cells did not correspond to ES cells but may have represented an incomplete state of reprogramming. While genetic experiments had established that Oct4 and Sox2 are essential for pluripotency (Chambers and Smith, *Oncogene*, 23:7150-7160 (2004); Ivanona et al., *Nature*, 442:5330538 (2006); Masui et al., *Nat Cell Biol*, 9:625-635 (2007)), the role of the two oncogenes c-myc and Klf4 in reprogramming is less clear. Some of these oncogenes may, in fact, be dispensable for reprogramming, as both mouse and human iPS cells have been obtained in the absence of c-myc transduction, although with low efficacy (Nakagawa et al., *Nat Biotechnol*, 26:191-106 (2008); Werning et al., *Nature*, 448:318-324 (2008); Yu et al., *Science*, 318: 1917-1920 (2007)).

MAPC

Human MAPCs are described in U.S. Pat. No. 7,015,037. MAPCs have been identified in other mammals. Murine MAPCs, for example, are also described in U.S. Pat. No. 7,015,037. Rat MAPCs are also described in U.S. Pat. No. 7,838,289.

These references are incorporated by reference for describing MAPCs first isolated by Catherine Verfaillie.

Isolation and Growth of MAPCs

Methods of MAPC isolation are known in the art. See, for example, U.S. Pat. No. 7,015,037, and these methods, along with the characterization (phenotype) of MAPCs, are incorporated herein by reference. MAPCs can be isolated from multiple sources, including, but not limited to, bone marrow, placenta, umbilical cord and cord blood, muscle, brain, liver, spinal cord, blood or skin. It is, therefore, possible to obtain bone marrow aspirates, brain or liver biopsies, and other organs, and isolate the cells using positive or negative selection techniques available to those of skill in the art, relying upon the genes that are expressed (or not expressed) in these cells (e.g., by functional or morphological assays such as those disclosed in the above-referenced applications, which have been incorporated herein by reference).

MAPCs have also been obtained my modified methods described in Breyer et al., *Experimental Hematology*, 34:1596-1601 (2006) and Subramanian et al., *Cellular Programming and Reprogramming: Methods and Protocols*; S. Ding (ed.), *Methods in Molecular Biology*, 636:55-78 (2010), incorporated by reference for these methods.

MAPCs from Human Bone Marrow as Described in U.S. Pat. No. 7,015,037

MAPCs do not express the common leukocyte antigen CD45 or erythroblast specific glycophorin-A (Gly-A). The mixed population of cells was subjected to a Ficoll Hypaque separation. The cells were then subjected to negative selection using anti-CD45 and anti-Gly-A antibodies, depleting the population of CD45+ and Gly-A+ cells, and the remaining approximately 0.1% of marrow mononuclear cells were then recovered. Cells could also be plated in fibronectin-coated wells and cultured as described below for 2-4 weeks to deplete the cells of CD45+ and Gly-A+ cells. In cultures of adherent bone marrow cells, many adherent stromal cells undergo replicative senescence around cell doubling 30 and a more homogenous population of cells continues to expand and maintains long telomeres.

Alternatively, positive selection could be used to isolate cells via a combination of cell-specific markers. Both positive and negative selection techniques are available to those of skill in the art, and numerous monoclonal and polyclonal antibodies suitable for negative selection purposes are also available in the art (see, for example, Leukocyte Typing V, Schlossman, et al., Eds. (1995) Oxford University Press) and are commercially available from a number of sources.

Techniques for mammalian cell separation from a mixture of cell populations have also been described by Schwartz, et al., in U.S. Pat. No. 5,759,793 (magnetic separation), Basch et al., 1983 (immunoaffinity chromatography), and Wysocki and Sato, 1978 (fluorescence-activated cell sorting).

Cells may be cultured in low-serum or serum-free culture medium. Serum-free medium used to culture MAPCs is described in U.S. Pat. No. 7,015,037. Commonly-used growth factors include but are not limited to platelet-derived growth factor and epidermal growth factor. See, for example, U.S. Pat. Nos. 7,169,610; 7,109,032; 7,037,721; 6,617,161; 6,617,159; 6,372,210; 6,224,860; 6,037,174; 5,908,782; 5,766,951; 5,397,706; and 4,657,866; all incorporated by reference for teaching growing cells in serum-free medium.

Additional Culture Methods

In additional experiments, the density at which MAPCs are cultured can vary from about 100 cells/cm$^2$ or about 150 cells/cm$^2$ to about 10,000 cells/cm$^2$, including about 200 cells/cm$^2$ to about 1500 cells/cm$^2$ to about 2000 cells/cm$^2$. The density can vary between species. Additionally, optimal density can vary depending on culture conditions and source of cells. It is within the skill of the ordinary artisan to determine the optimal density for a given set of culture conditions and cells.

Also, effective atmospheric oxygen concentrations of less than about 10%, including about 1-5% and, especially, 3-5%, can be used at any time during the isolation, growth and differentiation of MAPCs in culture.

Cells may be cultured under various serum concentrations, e.g., about 2-20%. Fetal bovine serum may be used. Higher serum may be used in combination with lower oxygen tensions, for example, about 15-20%. Cells need not be selected prior to adherence to culture dishes. For example, after a Ficoll gradient, cells can be directly plated, e.g., 250,000-500,000/cm$^2$. Adherent colonies can be picked, possibly pooled, and expanded.

In one embodiment, used in the experimental procedures in the Examples, high serum (around 15-20%) and low oxygen (around 3-5%) conditions were used for the cell culture. Specifically, adherent cells from colonies were plated and passaged at densities of about 1700-2300 cells/cm$^2$ in 18% serum and 3% oxygen (with PDGF and EGF).

In an embodiment specific for MAPCs, supplements are cellular factors or components that allow MAPCs to retain the ability to differentiate into cell types of more than one embryonic lineage, such as all three lineages. This may be indicated by the expression of specific markers of the undifferentiated state, such as Oct 3/4 (Oct 3A) and/or markers of high expansion capacity, such as telomerase.

Cell Culture

For all the components listed below, see U.S. Pat. No. 7,015,037, which is incorporated by reference for teaching these components.

In general, cells useful for the invention can be maintained and expanded in culture medium that is available and well-known in the art. Also contemplated is supplementation of cell culture medium with mammalian sera. Additional supplements can also be used advantageously to supply the cells with the necessary trace elements for optimal growth and expansion. Hormones can also be advantageously used in cell culture. Lipids and lipid carriers can also be used to supplement cell culture media, depending on the type of cell and the fate of the differentiated cell. Also contemplated is the use of feeder cell layers.

Cells in culture can be maintained either in suspension or attached to a solid support, such as extracellular matrix components. Stem cells often require additional factors that encourage their attachment to a solid support, such as type I and type II collagen, chondroitin sulfate, fibronectin, "superfibronectin" and fibronectin-like polymers, gelatin, poly-D and poly-L-lysine, thrombospondin and vitronectin. One embodiment of the present invention utilizes fibronectin. See, for example, Ohashi et al., Nature Medicine, 13:880-885 (2007); Matsumoto et al., *J Bioscience and Bioengineering*, 105:350-354 (2008); Kirouac et al., *Cell Stem Cell*, 3:369-381 (2008); Chua et al., *Biomaterials*, 26:2537-2547 (2005); Drobinskaya et al., *Stem Cells*, 26:2245-2256 (2008); Dvir-Ginzberg et al., *FASEB J*, 22:1440-1449 (2008); Turner et al., *J Biomed Mater Res Part B: Appl Biomater*, 82B:156-168 (2007); and Miyazawa et al., *Journal of Gastroenterology and Hepatology*, 22:1959-1964 (2007)).

Cells may also be grown in "3D" (aggregated) cultures. An example is PCT/US2009/31528, filed Jan. 21, 2009.

Once established in culture, cells can be used fresh or frozen and stored as frozen stocks, using, for example, DMEM with 40% FCS and 10% DMSO. Other methods for preparing frozen stocks for cultured cells are also available to those of skill in the art.

Pharmaceutical Formulations

U.S. Pat. No. 7,015,037 is incorporated by reference for teaching pharmaceutical formulations. In certain embodiments, the cell populations are present within a composition adapted for and suitable for delivery, i.e., physiologically compatible.

Formulations would be oriented to degree of desired effect, such as reduction of inflammation, reduction of apoptosis, edema, etc., upregulation of certain factors, etc.

In some embodiments the purity of the cells for administration to an organ is about 100% (substantially homogeneous). In other embodiments it is 95% to 100%. In some embodiments it is 85% to 95%. Particularly, in the case of admixtures with other cells, the percentage can be about 10%-15%, 15%-20%, 20%-25%, 25%-30%, 30%-35%, 35%-40%, 40%-45%, 45%-50%, 60%-70%, 70%-80%, 80%-90%, or 90%-95%. Or isolation/purity can be expressed in terms of cell doublings where the cells have undergone, for example, 10-20, 20-30, 30-40, 40-50 or more cell doublings.

The choice of formulation for administering the cells will depend on a variety of factors. Prominent among these will be the species of donor/recipient, the nature of the organ being treated, the nature of other therapies and agents that are being administered, the optimum route for administration, survivability via the effective route, the dosing regimen, and other factors that will be apparent to those skilled in the art. For instance, the choice of suitable carriers and other additives will depend on the exact route of administration and the nature of the particular dosage form.

Final formulations of the aqueous suspension of cells/medium will typically involve adjusting the ionic strength of the suspension to isotonicity (i.e., about 0.1 to 0.2) and to physiological pH (i.e., about pH 6.8 to 7.5). The final formulation will also typically contain a fluid lubricant.

The skilled artisan can readily determine the amount of cells and optional additives, vehicles, and/or carrier in compositions to be administered in methods of the invention. Typically, any additives (in addition to the cells) are present in an amount of 0.001 to 50 wt % in solution, such as in phosphate buffered saline. The active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %.

In some embodiments cells are encapsulated for administration, particularly where encapsulation enhances the effectiveness or provides advantages in handling and/or shelf life. Cells may be encapsulated by membranes, as well as capsules. It is contemplated that any of the many methods of cell encapsulation available may be employed.

A wide variety of materials may be used in various embodiments for microencapsulation of cells. Such materials include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers.

Techniques for microencapsulation of cells that may be used for administration of cells are known to those of skill in the art and are described, for example, in Chang, P., et al., 1999; Matthew, H. W., et al., 1991; Yanagi, K., et al., 1989; Cai Z. H., et al., 1988; Chang, T. M., 1992 and in U.S. Pat. No. 5,639,275 (which, for example, describes a biocompatible capsule for long-term maintenance of cells that stably express biologically active molecules). Additional methods of encapsulation are in European Patent Publication No. 301,777 and U.S. Pat. Nos. 4,353,888; 4,744,933; 4,749,620; 4,814,274; 5,084,350; 5,089,272; 5,578,442; 5,639,275; and 5,676,943. All of the foregoing are incorporated herein by reference in parts pertinent to encapsulation of cells.

Certain embodiments incorporate cells into a polymer, such as a biopolymer or synthetic polymer. Examples of biopolymers include, but are not limited to, fibronectin, fibrin, fibrinogen, thrombin, collagen, and proteoglycans. Other factors, such as the cytokines discussed above, can also be incorporated into the polymer. In other embodiments of the invention, cells may be incorporated in the interstices of a three-dimensional gel. A large polymer or gel, typically, will be surgically implanted. A polymer or gel that can be formulated in small enough particles or fibers can be administered by other common, more convenient, non-surgical routes.

The dosage of the cells will vary within wide limits and will be fitted to the individual requirements in each particular case. The number of cells will vary depending on the type, weight, and condition of the organ, the number or frequency of administrations, and other variables known to those of skill in the art. The cells can be administered by a route that is suitable for the tissue or organ. Examples of suitable delivery routes can include intra-tracheal delivery (e.g., for lung), intravenous delivery, intra-arterial delivery (e.g., intra-coronary), direct injection into the organ, and intra-lymphatic system delivery.

The cells can be suspended in an appropriate excipient in a concentration from about 0.01 to $1 \times 10^5$ cells/ml, about $1 \times 10^5$ cells/ml to $10 \times 10^6$ cells/ml, or about $10 \times 10^6$ cells/ml to $5 \times 10^7$ cells/ml. Suitable excipients are those that are biologically and physiologically compatible with the cells and with the recipient organ, such as buffered saline solution or other suitable excipients. The composition for administration can be formulated, produced, and stored according to standard methods complying with proper sterility and stability.

Dosing

Doses (i.e., the number of cells) for humans or other mammals can be determined without undue experimentation by the skilled artisan, from this disclosure, the documents cited herein, and the knowledge in the art. The optimal dose to be used in accordance with various embodiments of the invention will depend on numerous factors, including the following: the disease being treated and its stage; the species of the donor, their health, gender, age, weight, and metabolic rate; the donor's immunocompetence; other therapies being administered; and expected potential complications from the donor's history or genotype. The parameters may also include: whether the cells are syngeneic, autologous, allogeneic, or xenogeneic; their potency; the site and/or distribution that must be targeted; and such characteristics of the site such as accessibility to cells. Additional parameters include co-administration with other factors (such as growth factors and cytokines). The optimal dose in a given situation also will take into consideration the way in which the cells are formulated, the way they are administered (e.g., perfusion, intra-organ, etc.), and the degree to which the cells will be localized at the target sites following administration.

Ultimately, the dose levels, timing, and frequency would be determined by effectiveness. This will be measured by organ health and viability, and possibly by organ function and clinical measures post-transplant. Such measures will vary by organ. In one embodiment, they could include organ function measures. One could access measures of organ viability for transplant via the clinical literature. In another embodiment, the level(s) or pattern(s) of certain markers (e.g., tissue mRNA levels, cytokine levels, and inflammatory cell numbers) can be assayed (e.g., using qPCR) to determine effectiveness. For example, the level of IL-10 mRNA from pulmonary tissue can be assayed by qPCR to determine effectiveness. In another example, one might evaluate dose in lung by impact on: cytokine levels; other inflammatory markers in fluids (e.g., obtained by bronchoalveolar lavage); edema levels; hemodynamic and ventilator measures; and evaluation of gas exchange in ex vivo (re)perfused lungs.

In various embodiments, cells/medium may be administered in an initial dose, and thereafter maintained by further administration. Cells may be administered by one method initially, and thereafter administered by the same method or one or more different methods. The levels can be maintained by the ongoing administration of the cells/medium. Various embodiments administer the cells either initially or to maintain their level in the subject or both by intravenous injection. In a variety of embodiments, other forms of administration are used, dependent upon the type and condition of the organ and other factors, discussed elsewhere herein.

Cells/medium may be administered in many frequencies over a wide range of times. Generally lengths of treatment will be proportional to the length of the collection and handling process, the effectiveness of the therapies being applied, and the condition and response of the organ being treated.

In other embodiments, cells can be administered (e.g., by intravenous, intra-arterial, intra-tracheal, direct injection, etc.) to a donor subject prior to organ harvest. Depending upon the route of administration, the cells can be administered for a suitable period of time (e.g., minutes to about 1-4 hours, about 4-8 hours, about 8-12 hours, about 12-16 hours, about 16-20 hours, about 20-24 hours). The organ can be harvested after the period of time by conventional surgical technique(s). After harvest, cells are contacted (e.g., immediately contacted) with the organ for a time sufficient to allow the cells to distribute throughout the organ (e.g., less than about 1 hour, about 1-2 hours, about 2-3 hours, about 3-4 hours). Cells can be contacted with the organ by infusion and/or immersion of the organ into a bath containing the cells. Next, the organ can be stored on ice and/or attached to a reperfusion system, whereafter the organ is delivered to the transplantation site.

Upon arrival at the transplantation site, the organ can be placed on a reperfusion system (if it has not been done so already) containing the cells. The organ can then be infused with the cells for a period of time (e.g., less than about an hour, about 1-2 hours, about 2-3 hours, about 3-4 hours) depending upon the organ and the reperfusion system. During transplantation, cells can be contacted with the organ by infusion into the recipient (e.g., intravenously), direct injection into the organ, and/or direct application to a surface of the organ. Infusion can be done, for example, prior to closure of the vessel(s) entering and exiting the organ. During liver transplantation, for instance, cells may be infused into the hepatic portal vein prior to attachment of the vein to the transplanted liver. Additionally or alternatively, cells can be delivered to the organ after transplantation (e.g., after closure of the vessel(s) entering and exiting the organ) for a suitable period of time (e.g., minutes to about 1-4 hours, about 4-8 hours, about 8-12 hours, about 12-16 hours, about 16-20 hours, about 20-24 hours) depending upon the delivery system and the organ.

Compositions

The invention is also directed to cell populations with specific potencies for achieving any of the effects described herein. As described above, these populations are established by selecting for cells that have desired potency. These populations are used to make other compositions, for example, a cell bank comprising populations with specific desired potencies and pharmaceutical compositions containing a cell population with a specific desired potency.

EXAMPLE

Methods

Lung Harvest and Ex Vivo Perfusion

Following research consent obtained by the local Organ Procurement Agency, LifeGift, the discarded donated lungs were procured for this study under an established IRB protocol at the Houston Methodist (IRB(2)1111-0205). Lungs from each of the five patients were procured in a standard fashion with antegrade Perfadex (Vitrolife AB, Gothenburg, Sweden) 60 ml/Kg flush plus retrograde Perfadex perfusion through the pulmonary veins. The lungs were then stored in plastic bags containing 1 liter of Perfadex and were kept on ice during transport. Once the lungs arrived at the Houston Methodist, they were then stored in a refrigerator @ 4° C. for a total 8 hours of cold static storage in order to induce cold ischemic injury.

Ex Vivo Lung Perfusion (EVLP) was performed with the CE-marked Vivoline LS1 (Vivoline Medical AB, Lund, Sweden) (FIG. 1) (Wierup, P. et al., *Ann Thorac Surg* 2006; 81(2):460-6; Ingemansson, R. et al., *Ann Thorac Surg* 2009; 87(1):255-60; and Cypel, M. et al., *N Engl J Med* 2011; 364(15):1431-40). The system was primed with 2.5 L of Steen Solution (XVIVO Perfusion). The use of washed red blood cell or blood was avoided in order to decrease the number of variables in the feasibility study. Meropenem 100 mg (AstraZeneca AB, Sodertalje, Sweden) and 10,000 U of Heparin (LEO Pharmaceutical, Copenhagen, Denmark) were added to the perfusate. Before the lungs were connected to the EVLP unit, the pH in the solution was corrected to between 7.35 and 7.45 using trometamol (Addex-THAM, Fresenius Kabi AB, Uppsala, Sweden). In one case where the heart was procured as well, a Dacron Graft was sutured to the divided pulmonary artery branches in order to reconstitute the integrity of the pulmonary artery (PA) and facilitate the connection of the lung to the EVLP circuit. The trachea was connected to the mechanical ventilator via a silicon tube size matching the tracheal diameter. A temperature probe was positioned inside the left atrium. Initially, for de-airing the circuit, the lungs were perfused at a flow rate of 0.5 L/min. The shunt for de-airing on the inflow cannula was kept open until the organ reached 32° C. and then closed for the rest of the session. The flow was then increased to 100% of estimated cardiac output for the specific set of lungs. The lungs were then warmed over 30 minutes to a target of 36° C. and the temperature difference between lung blood inflow and outflow was not allowed to exceed 8° C. The flow rate was then increased gradually to a target level of 70 mL/min per kilogram donor weight, during which the PA pressure was measured continuously and limited to 15 mm Hg. Rewarming was achieved within 20-30 minutes. When the perfusate temperature reached 32° C., mechanical ventilation was started in volume-controlled mode at an initial tidal-volume of 3 ml per kilogram of donor weight with a positive end-expiratory pressure (PEEP) level of 5 cm H$_2$O, a rate of 7-10 breaths/min, and a FiO$_2$ of 0.5. Tidal volume was then increased gradually to a maximum of 7 mL per kilogram of donor weight. Perfusate samples for blood gas analyses were drawn from the dedicated port of the system.

Cells

Human bone marrow derived MAPCs (Human Multi-Stem®, Athersys Inc., Cleveland) were isolated from a single bone marrow aspirate, obtained with consent from a healthy donor, and processed according to previously described methods (Penn, M S et al., *Circ Res* 2012; 110(2):304-11; Maziarz, R T et al., *Biology of Blood and Marrow Transplantation* 2012; 18(2 Sup):5264-5265; and clinicaltrials.gov #NCT01436487, #NCT01240915 and #NCT01841632). In brief, MAPCs were cultured in fibronectin-coated plastic tissue culture flasks under low oxygen tension in a humidified atmosphere of 5% CO$_2$. Cells were cultured in MAPC culture media (low-glucose DMEM [Life Technologies Invitrogen] supplemented with FBS (Atlas Biologicals, Fort Collins, Colo.), ITS liquid media supplement [Sigma], MCDB [Sigma], platelet-derived growth factor (R&D Systems, Minneapolis, Minn.), epidermal growth factor (R&D Systems), dexamethasone ([Sigma], penicillin/streptomycin [Life Technologies Invitrogen], 2-Phospho-L-ascorbic acid [Sigma, St. Louis, Mo.), and linoleic acid-albumin (Sigma). Cells were passaged every 3-4 d, harvested using trypsin/EDTA (Life Technologies Invitrogen, Carlsbad, Calif.). The cells were positive for CD49c and CD90 and negative for MHC class II and CD45 (all Abs were from BD Biosciences, Franklin Lakes, N.J.). Cells were subsequently frozen at population doubling 30-35 in cryovials in the vapor phase of liquid nitrogen at a concentration of 1-10×10$^6$ in 1 ml (PlasmaLyte, 5% HSA and 10% DMSO). Immediately prior to their use, MAPCs were thawed and used directly.

Cell Inoculations, Lung Incubations, and Bronchoalveolar Lavage (BAL) Fluid and Tissue Analyses When the temperature as measured by the intra-atrial probe reached approximately 32° C., MultiStem 1 ml vials were thawed, diluted into 19 ml of sterile saline and administered by bronchoscope into the proximal portion of the LLL bronchus. A similar volume of vehicle (20 ml of sterile saline) was similarly inoculated into the proximal portion of the RLL bronchus. Five minutes after delivery of MultiStem, the lungs were connected to a Hamilton-C2 mechanical ventilator. After either 2 or 4 hours of perfusion on the Vivoline system the experiments were stopped. Five minutes before stopping the perfusion, the same subsegments of the RLL and LLL that had been previously inoculated with either cells or vehicle were lavaged with 60 mL saline. The recovered BAL fluid was then separated into aliquots of either raw BAL fluid for assessing total cell counts and cell differentials or was centrifuged (1200 g×10 min at 4° C.) and the supernatant was collected in separate tubes, snap frozen, and stored at −70° C. (Lathrop, M J et al., *Stem Cells Translational Medicine* (in press); and Goodwin, M. et al., *Stem Cells* 2011:29(7):1137-48). For one lung, BAL fluid samples were also obtained during rewarming phase before ventilation was started, just prior to MSC or vehicle delivery.

Total BAL fluid cell numbers were determined using an ADVIA® Hematology Analyzer (Siemens Diagnostics, Johnson City, Tenn.). Cytospins were made using 5×10$^4$ cells centrifuged onto pre-cleaned, pre-treated glass slides (Corning Incorporate, Corning, N.Y.) at 800 rpm for 8 min, dried overnight, and stained using DiffQuick (Hema 3 Stain Set, Fisher Scientific, Pittsburgh, Pa.). Cell populations were determined by blinded manual count of 200 cells performed by three separate individuals (Lathrop, M J et al., *Stem Cells Translational Medicine* (in press); and Goodwin, M. et al., *Stem Cells* 2011:29(7):1137-48). Protein content in undiluted BAL fluid was assessed by Bradford assay (Bio-Rad, Hercules, Calif.). The Human Cytokine Array Kit, Panel A (R&D Systems, Minneapolis, Minn.) was used to examine BAL fluid supernatants for soluble cytokines, chemokines, and other substances including C5/Ca, CD40L, CD54, CXCL1, CXCL10, G-CSF, Gro-1α, IL-1α, IL-1β, IL-1RA, IL-6, IL-8, IL-10, IL-16, IL-23, IP-10, I-TAC, MCP-1, MIF, PAI-1, RANES, serpin E1, sICAM, sTREM-1, TNFα, and the relative amount of cytokine compared to internal controls determined on a UVP Bioimaging system. (Upland, Calif.). Elisas for other specific cytokines were performed according to manufacturer's instructions, IL-10 (R&D Systems, Minneapolis, Minn., Cat #:D1000B), and STC1, TSG-6 and iNOS (MyBioSource, San Diego, Calif., Cat #s: MBS946255, MBS926793, MBS723617).

Histological Assessments

Following BAL at the end of the perfusion period, the lungs were subsequently gravity fixed with 10% formalin at room temperature for 1 hour. Fixed lungs were dissected and the areas where cells were instilled stored in 10% formalin prior to paraffin fixation. Mounted 5 μm sections were then evaluated for histologic appearance. Lung inflammation was scored on 10 airways per animal, in a blinded fashion by three individuals, based on the presence and intensity of peri-bronchial cell infiltrates compared to known positive and negative controls using an established semi-quantitative scoring system, using a 0-3 range and 0.5 scale increments as previously described (Lathrop, M J et al., Stem Cells Translational Medicine (in press); and Goodwin, M. et al., Stem Cells 2011:29(7):1137-48).

qPCR Analyses of Tissue Inflammatory Markers

Lung biopsy samples from lungs 2-5 were obtained using an automatic stapler (Covidien GIA™ DST Series™ 80 mm) from the periphery of the LLL and RLL just prior to cell or vehicle infusion at 2 and 4 hours after cell or vehicle infusion and at the end of the experiment. The samples were snap frozen and subsequently homogenized and the expression levels of inflammatory cytokine mRNAs determined by qPCR (see details below).

Samples were homogenized in RNA lysis buffer and RNA extracted using the RNeasy kit (Qiagen, Germantown, Md.) according to manufacturer's instructions. Additional DNase treatment was performed using the DNA-free kit (Life Technologies, Carlsbad, Calif.). RNA concentration was measured by NanoDrop 2000 (Thermo Scientific, Waltham, Mass.) and 1 μg RNA was reverse transcribed using M-MLV Reverse Transcriptase (Promega, Madison, Wis.) followed by RNAse treatment using RNace-it Cocktail (Agilent, Santa Clara, Calif.). Reverse transcriptase negative samples and water were run as controls. 5 μl of the cDNA was mixed with SYBR green (Promega) and primers (IDT) and run on the ABI 7500 FAST system (Applied Biosystems, Foster City, Calif.). The samples were normalized to GAPDH and expressed as a percent of Human Reference (Agilent)+/− standard deviation.

Primer sequences were as follows:

VEGFA-F1 (SEQ ID NO: 1);
VEGFA-R1 (SEQ ID NO: 2);
IGF1-F4 (SEQ ID NO: 3);
IGF1-R4 (SEQ ID NO: 4);
EGF-F1 (SEQ ID NO: 5);
EGF-R1 (SEQ ID NO: 6);
IL-10-F2 (SEQ ID NO: 7);
IL-10-R2 (SEQ ID NO: 8);
FGF2-F1 (SEQ ID NO: 9);

-continued

FGF2-R1 (SEQ ID NO: 10);
HGF-F1 (SEQ ID NO: 11);
HGF-R1 (SEQ ID NO: 12);
CCL5-F1 (SEQ ID NO: 13);
CCL5-R1 (SEQ ID NO: 14);
TGFB1-F1 (SEQ ID NO: 15);
TGFB1-R1 (SEQ ID NO: 16);
CXCL10-F1 (SEQ ID NO: 17);
CXCL10-R1 (SEQ ID NO: 18);
NOS3-F2 (SEQ ID NO: 19);
NOS3-R2 (SEQ ID NO: 20);
STC1-F1 (SEQ ID NO: 21);
STC1-R1 (SEQ ID NO: 22);
GAPDH-F1 (SEQ ID NO: 23);
GAPDH-R1 (SEQ ID NO: 24);
ANGPT1-F2 (SEQ ID NO: 25);
ANGPT1-R2 (SEQ ID NO: 26);
NOS2-F1 (SEQ ID NO: 27);
NOS2-R1 (SEQ ID NO: 28);

-continued

TNFAIP6-F1 (SEQ ID NO: 29);
TNFAIP6-R1 (SEQ ID NO: 30);
FGF7-F1 (SEQ ID NO: 31);
and
FGF7-R1 (SEQ ID NO: 32).

Statistical Analysis

Groups were compared using either one way or two-way ANOVA with a Fishers LSD post-test or by direct analysis between two groups by Student's T-test, using a Welch's correction for unequal variances, as appropriate (Lathrop, M J et al., *Stem Cells Translational Medicine* (in press); and Goodwin, M. et al., *Stem Cells* 2011: 29(7): 1137-48).

Results

The relevant clinical characteristics of the donor lungs are summarized in Table 1.

TABLE 1

Clinical Characteristics of the Donor Lungs

| Donor Characteristics | 1 | 2 | 3 | 4 | 5 | Mean ± SD |
|---|---|---|---|---|---|---|
| Age | 55 | 56 | 44 | 66 | 50 | 54.2 ± 3.6 |
| Sex | Male | Male | Male | Female | Male | |
| Cause of Death | CVA | SH | Asphyxiation | IH | MVA | |
| $PaO_2$ @100% $FiO_2$ | 150 | 186 | 254 | 443 | 149 | 236.4 ± 55.1 |
| Peep | 10 | 10 | 10 | 5 | 10 | 9.0 ± 1.0 |
| Radiographic Findings | Infiltrate-Edema | Infiltrate-Edema | Infiltrate-Edema | Clear | Edema-Right lower lobe collapse, Right pleural effusion | |
| Lung Appearance | Edematous | Edematous | Edematous | Multiple surface nodules | Contusions, Edematous | |

CVA: Cerebrovascular accident; SH: Subarachnoid hemorrhage; IH: Intracranial Hemorrhage; MVA: motor vehicle accident.

Donor age ranged from 44-66 and three of the five donor lungs were obtained from patients with devastating neurologic events, one from asphyxia, and one from a motor vehicle accident. Four of the five lungs were not deemed suitable for transplant because of poor functional status including low $PaO_2$ values with a mean of 184.75 mmHg at 100% $FiO_2$ at ±a PEEP of 10 mmHg. These lungs also had radiographic abnormalities, variously including contusions, significant emphysema, or lobar collapse that did not respond to recruitment maneuvers in the operating room. Each of these lungs also had radiographic signs of pulmonary edema with two having also pleural effusion and all were noted to be variably edematous following surgical removal. Lung #5 had RLL collapse on CXR but expanded following removal and bronchoscopic removal of mucus plugs. One lung (lung #4) was physiologically suitable for donation with normal appearance, clear CXR, and good oxygenation on 5 mmHg PEEP but not utilized due to the presence of small surface nodules that were subsequently found to be benign on biopsy.

A summary of the protocol utilized for each lung is presented in Table 2 and also in schematic form in FIG. 1.

TABLE 2

Summary of Experimental Protocol

| Donor Lung | 1 | 2 | 3 | 4 | 5 | Mean ± SD |
|---|---|---|---|---|---|---|
| Duration of Cold Static Storage (hours) | 8 | 8 | 8 | 8 | 8 | 8.0 ± 0 |
| Rewarming Time (minutes) | 22 | 25 | 28 | 26 | 24 | 25.0 ± 1.0 |
| Duration of Ex Vivo Perfusion (hours) | 4 | 2.5 | 4 | 4 | 4 | 3.6 ± 0.6 |
| Cells or Vehicle Delivered | $10^7$ MSC to LLL Vehicle to RLL | $10^7$ MSC to LLL Vehicle to RLL | $10^7$ MSC to LLL Vehicle to RLL | $10^6$ MSC to LLL Vehicle to RLL | $10^7$ MSC to LLL Vehicle to RLL | |

Figure 2:
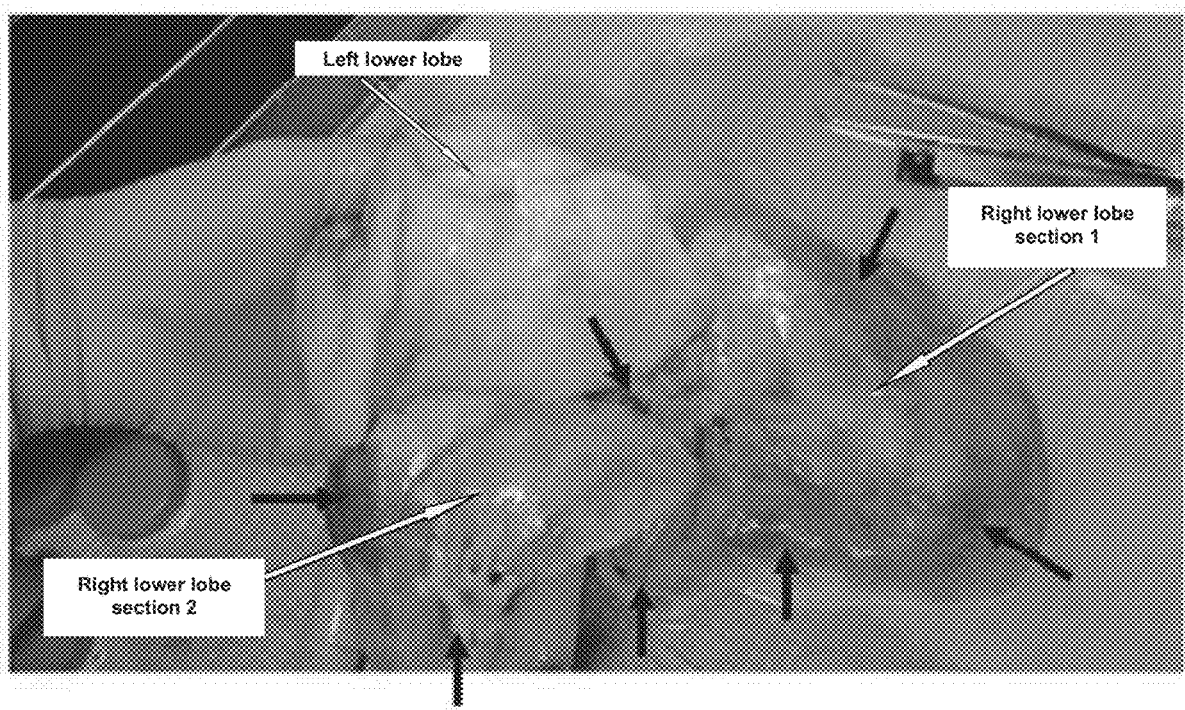
FIG. 2. Representative gross appearances of the right lower lobe (RLL) and left lower lobe (LLL) of lung 2 following reperfusion. The MSC-treated LLL appears normal while the vehicle-treated RLL appears edematous and inflamed.

Overall the lungs had similar cold storage (8 hrs) and rewarming (25+2.2 minutes) times and subsequently similar reperfusion times (3.7±0.6 hours) following bronchoscopic administration of cells or vehicle. At the end of the reperfusion period, there was some degree of further edema that had developed in each lung and lung number 4 had also newly developed some degree of edema. However, overall there was less visible edema and inflammation in the MSC-treated (LLL) vs. vehicle-treated (RLL) lobes, even with the lower dose of MAPCs utilized in lung #4. Representative images are shown in FIG. 2.

Figure 3:
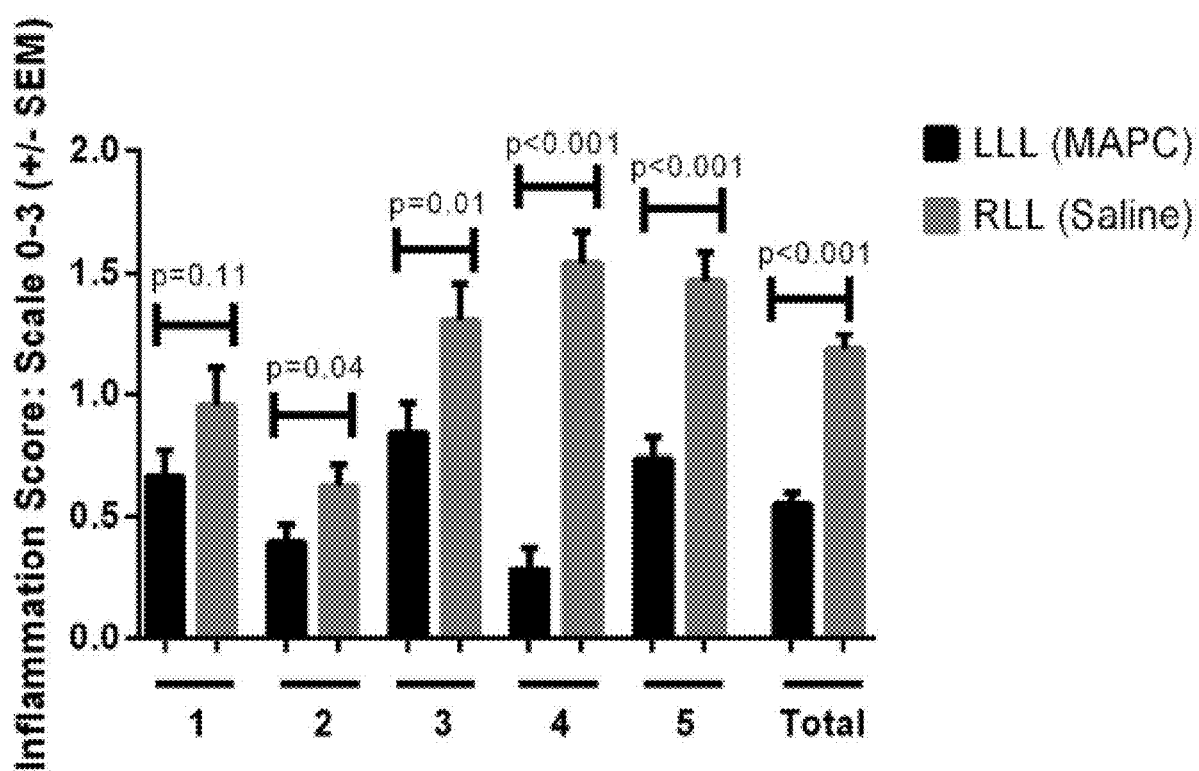
FIG. 3. Semi-quantitative scoring demonstrates significant decrease in overall inflammation in the MSC-treated LLL compared to the vehicle-treated RLL in 4 out of 5 lungs and in aggregate. Means±SD of pooled observations from 3 blinded observers are depicted.
Figure 4A:
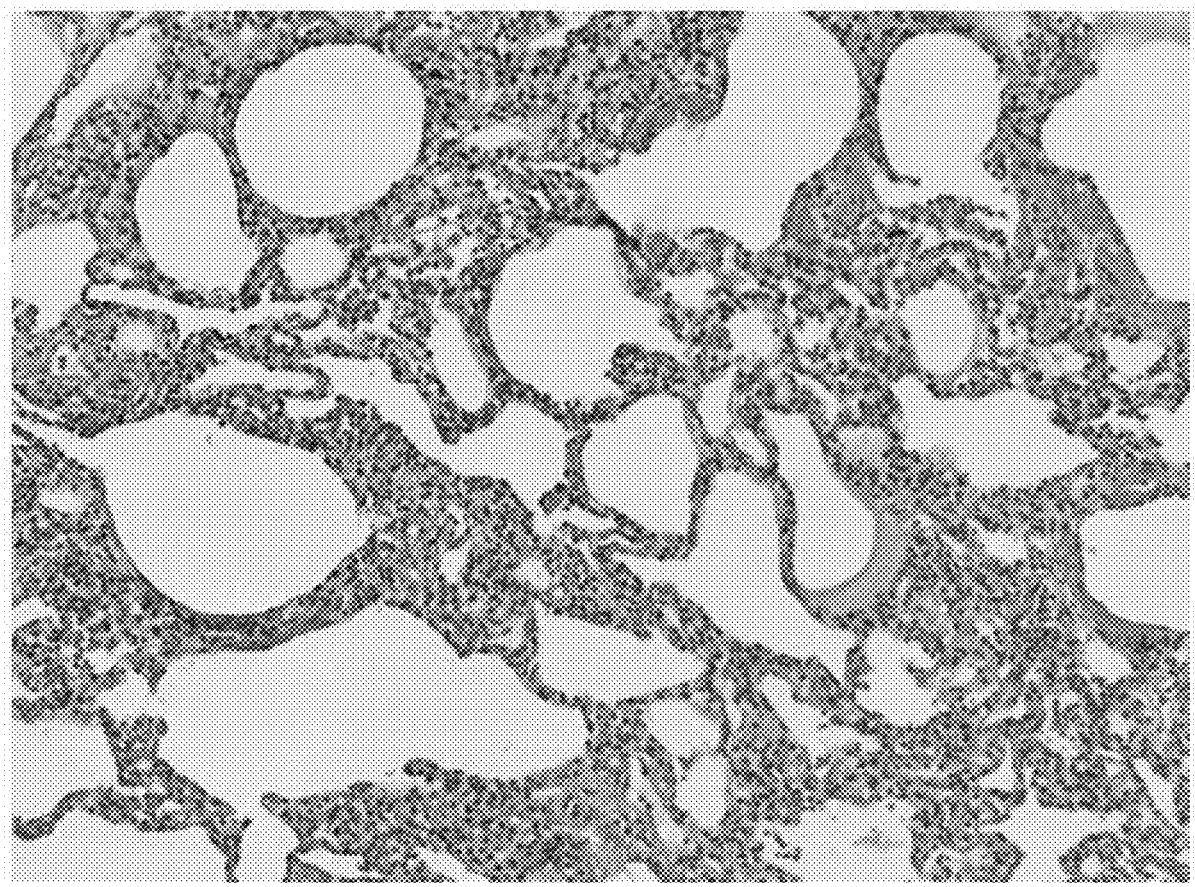
FIGS. 4A-B. Representative photomicrographs from lung 1 demonstrate minimal to no significant inflammation in MSC-treated LLL vs. alveolar septal thickening, edema, and perivascular (FIG. 4A) and peri-bronchial inflammatory cell infiltrates (FIG. 4B). Original Mag 200×.
Figure 4B:
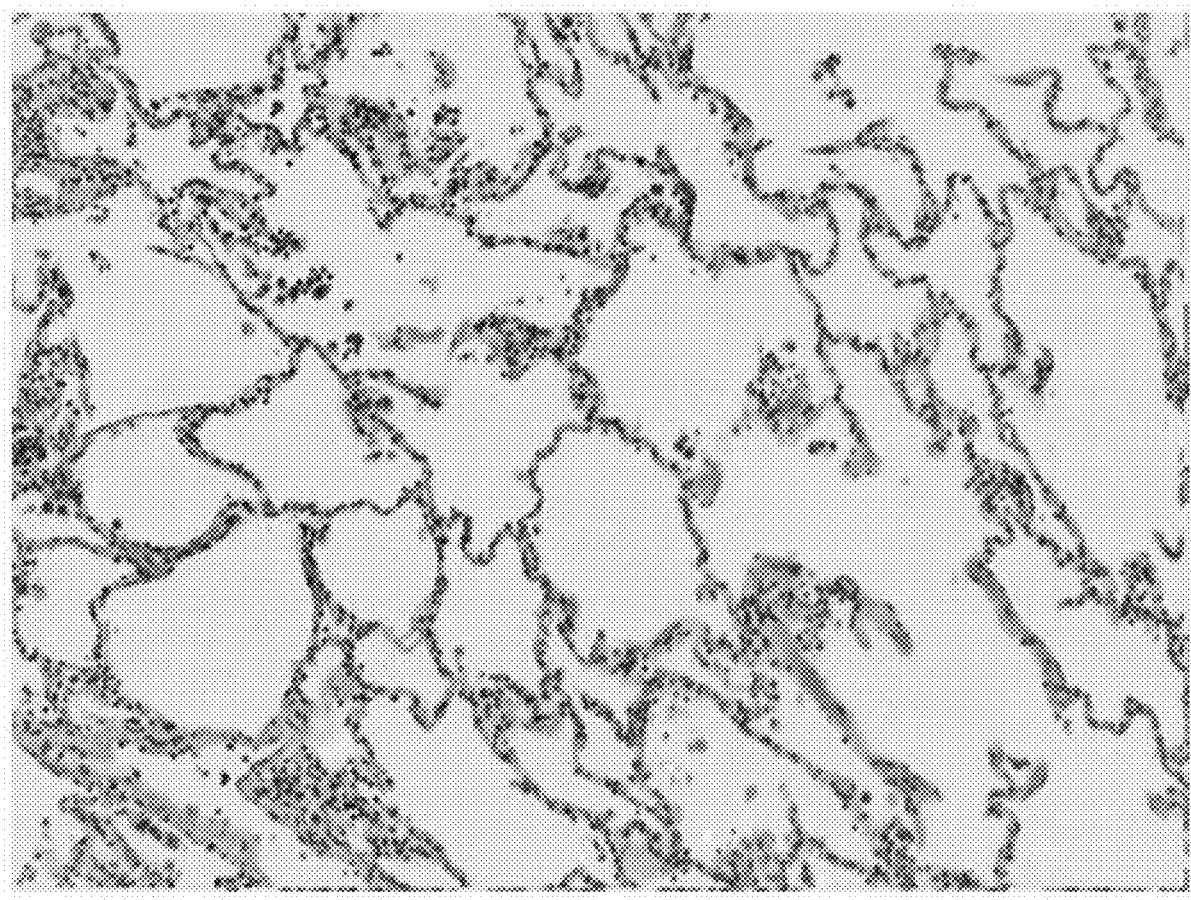

Histologic assessment of the lungs at the end of the reperfusion period demonstrated that although patches of inflamed areas could be found in some of the MAPC-treated LLLs, there was significantly less overall inflammation in 4 out of the 5 lungs and also averaged over all 5 lungs, as assessed by semi-quantitative scoring of peribronchial, perivascular, and alveolar septa edema and by presence of inflammatory cell infiltrates (FIG. 3). Representative photomicrographs are depicted in FIG. 4.

Figure 5A:
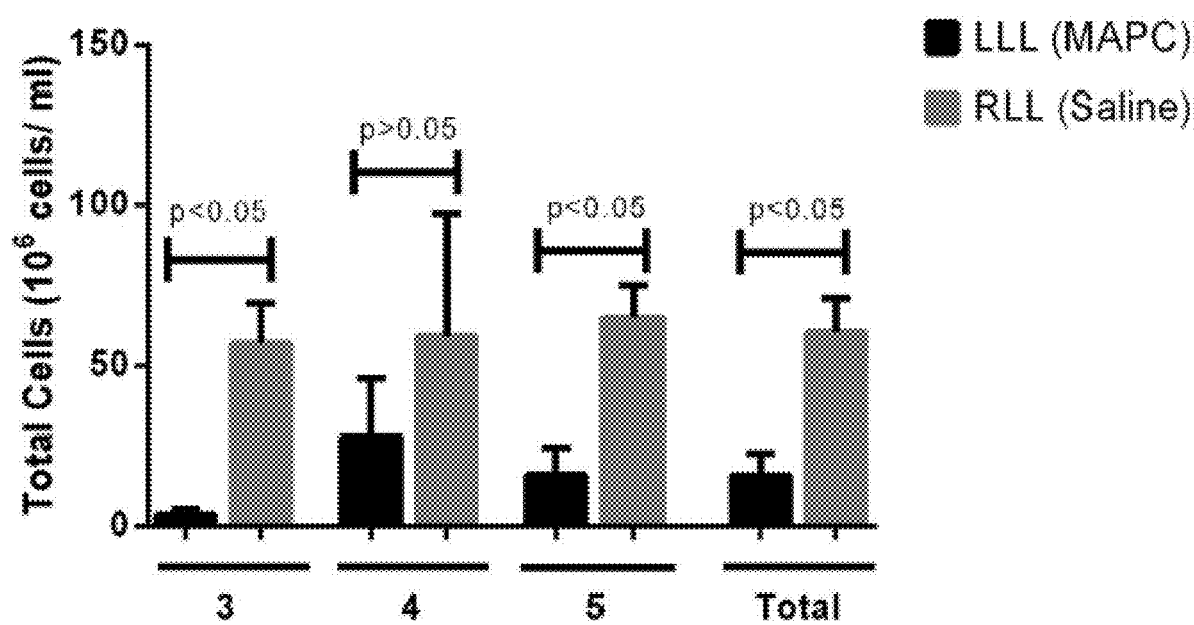
FIGS. 5A-C. Decrease in total BAL fluid cell counts in the MSC-treated LLL in lungs 3-5 (FIG. 5A). Total cell counts were not assessed in lungs 1 or 2. MSC instillation also resulted in a significant decreased in the elevated numbers of BAL fluid total neutrophils and eosinophils in all 5 lungs (FIGS. 5B-C). Data represents means±SEM of pooled observations from 3 blinded observers.
Figure 5B:
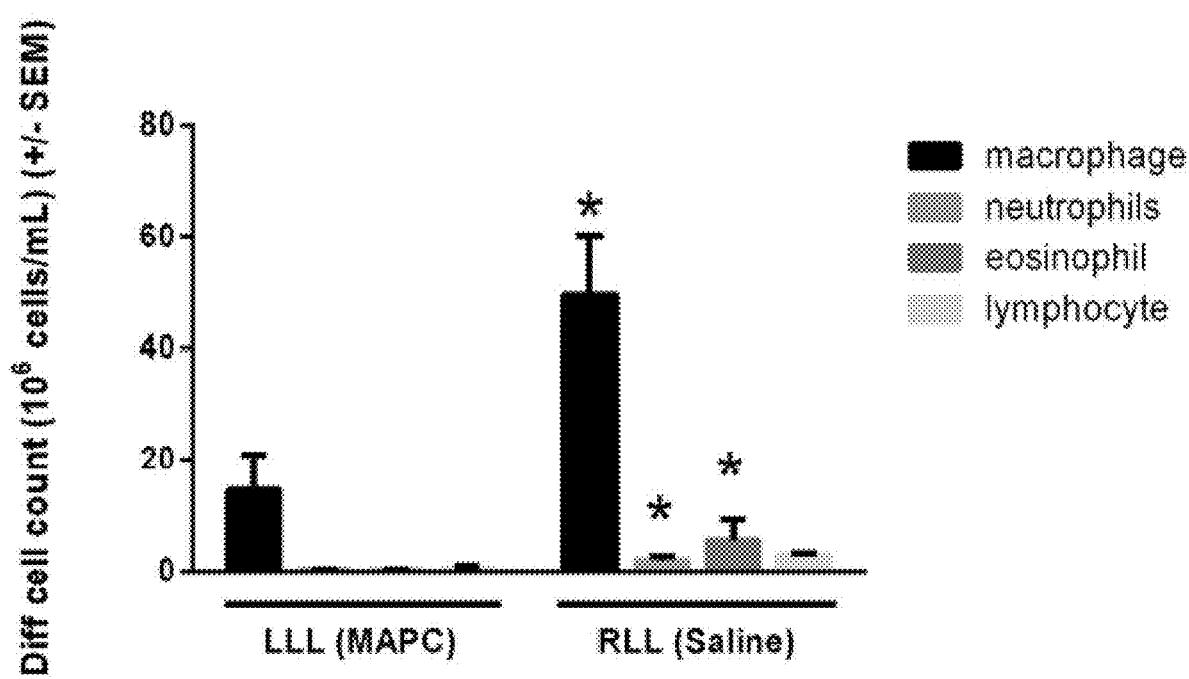
Figure 5C:
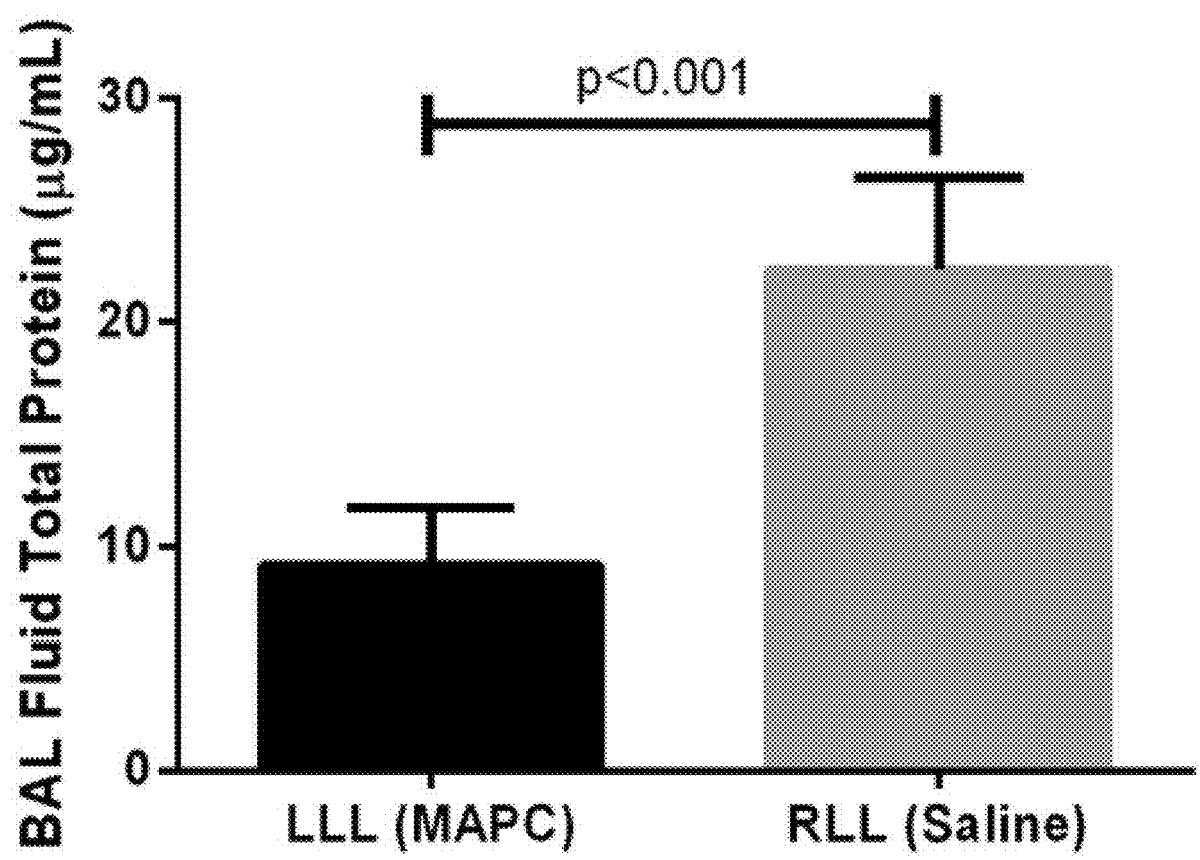

Total BAL fluid cell counts were obtained in two out of four lungs (lungs 3 and 5) receiving the higher cell dose. In both cases, there was a significant decrease in the MSC-treated LLL compared to the vehicle-treated RLL (FIG. 5A). A trend towards decrease in total BAL fluid cell counts was also observed in the lung receiving the lower MSC dose (lung 4, FIG. 5A). Cell differentials obtained on BAL fluid samples from all five lungs demonstrated a consistent increase in neutrophils and eosinophils in the vehicle-treated RLL that was ameliorated in the MSC-treated LLL (FIG. 5B). Measurements of BAL fluid total protein levels was variable between the lungs but a consistent decrease in total protein in the MSC-treated LLL vs. vehicle-treated RLL was observed in all 5 lungs (FIG. 5C).

Figure 6:
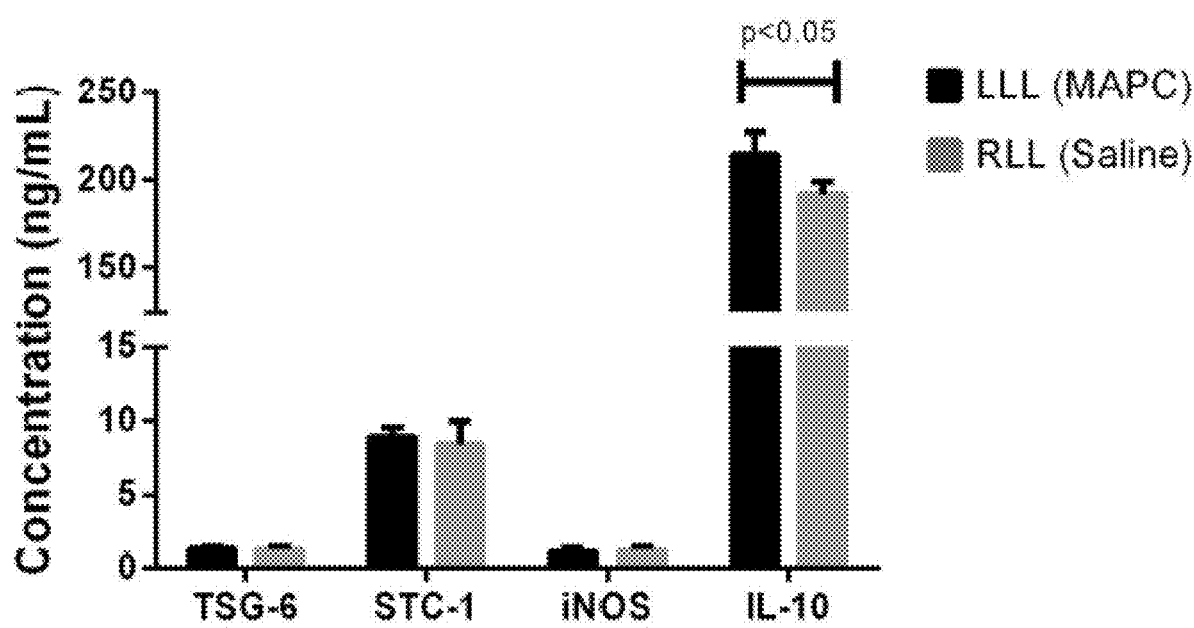
FIG. 6. Representative BAL fluid cytokine analyses from Lung 4 demonstrate significant increase in IL-10 in the MSC-treated LLL but no significant change in iNOS, STC-1, or TSG-6. Data represents means+standard deviations from triplicate determinations of each LLL or RLL sample.
Figure 7:
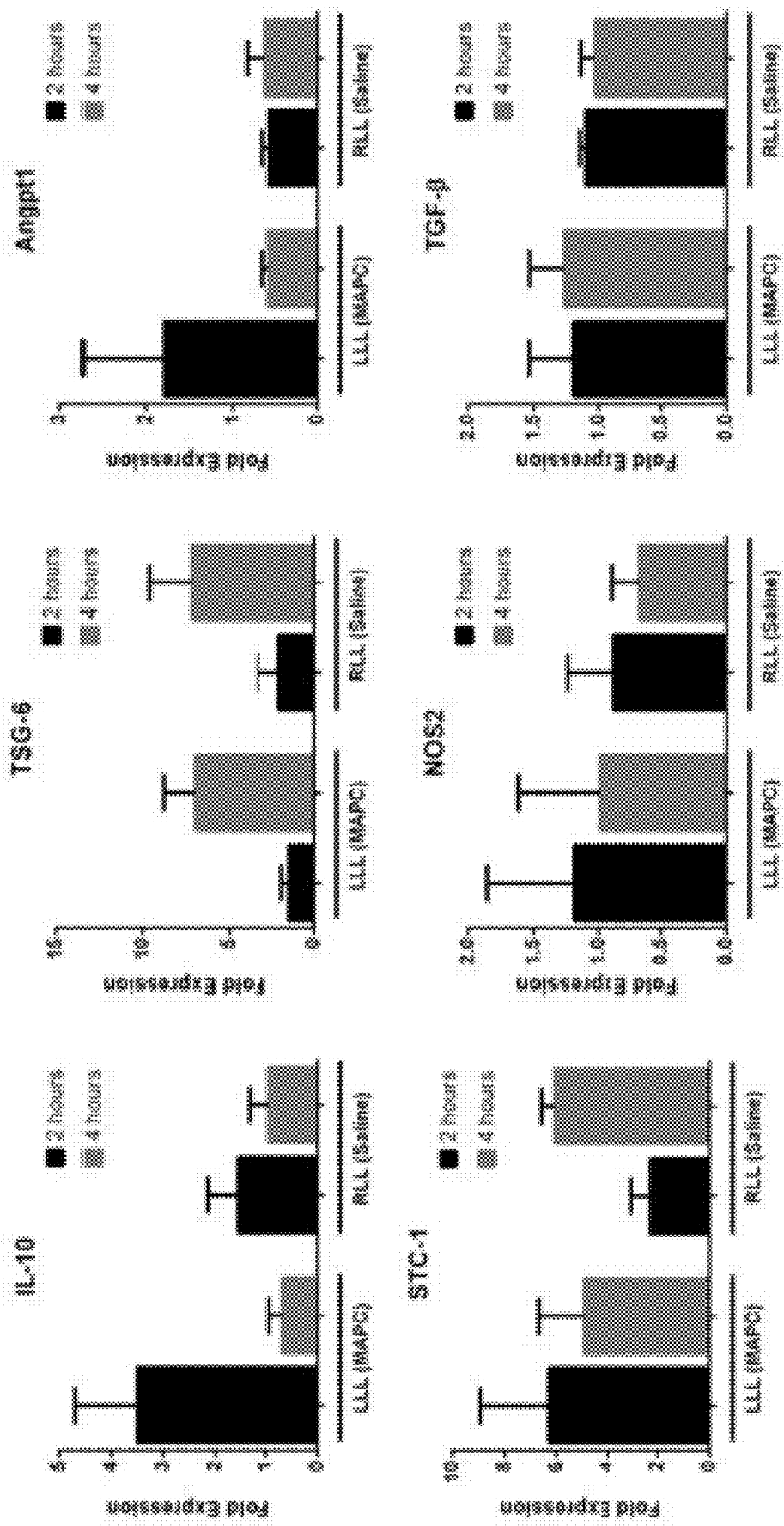
FIG. 7. Cytokine analysis of lung tissue. qPCR analysis was performed on the lung tissue samples collected from the LLL and RLL of lungs 2-5 at t=0, 2 and/or 4 hours. The fold-expression represents the levels of the target gene compared to the t=0 value. All data were normalized to a housekeeping gene, GAPDH. Data represents means+standard deviations from LLL and RLL samples from lungs 2-5.

An increase in levels of IL-10 in the MSC-treated LLL compared the vehicle treated RLL was observed (FIG. 6). However, other soluble anti-inflammatory mediators implicated in pre-clinical models of MSC actions in lung injury and other models, such as IL-1RA, STC, TGS-6, and iNOS, were not reliably increased in the MSC-treated LLL in any of the 5 lungs (FIG. 6). Tissue mRNA levels were assessed in 4 of 5 lungs (lungs 2-5) by qPCR analyses of biopsy samples obtained prior to cell or vehicle administration and then after either 2 or 4 hours of reperfusion period. Overall, patterns of tissue mRNA levels were more consistent between the 4 lungs. Comparable to BAL fluid levels of IL-10 protein, there was a 3.5-fold increase in the levels of tissue IL-10 mRNA in the MSC-treated LLL compared to only a 1.6-fold increase in vehicle-treated RLL as assessed at 2 hrs (FIG. 7). Similar increases in LLL vs. RLL were also observed at 2 hrs in mRNA levels of Angpt1 and STC1. Interestingly, for both the LLL and RLL there was a large increase in the fold expression of TSG6 from 2 to 4 hours.

Discussion

A number of different methods have been studied to improve the viability of donor lungs and to decrease either warm or cold ischemic inflammatory injury. These include a flushing solution with extracellular characteristics delivered both in an antegrade and retrograde fashion and the use of a portable ex vivo preservation system currently under clinical investigation for use in transport of donor lungs (Machuca, T N et al., *Surg Clin North Am* 2013; 93(6):1373-94). Different areas of research for therapeutic interventions aim to modulate the response induced by ischemia and reperfusion. For example experimental animal models have shown beneficial effect from gene therapy deliver of IL-10 (Cypel, M. et al., *Sci Transl Med.* 2009; 1(4):4-9) and from adenosine receptor activation (Fernandez, L G et al., *J Thorac Cardiovasc Surg* 2013; 145(6):1654-9; and Mulloy, D P et al., *Ann Thorac Surg* 2013; 95(5):1762-7). However, while the experimental data are promising, it is unlikely that modulating one out of many inflammatory pathways can regulate a phenomenon that alters several cellular mechanisms involved, as innate and adaptive immunity, the activation of the complement cascade, endothelial dysfunction, and the triggering of cell death. In contrast, bone marrow-derived MSCs and MAPCs have the unique potential of acting on multiple inflammatory pathways involved in ischemia/reperfusion injury.

Ex vivo lung perfusion (EVLP) was originally designed as a method to assess the quality of lungs from donation after cardiac death (DCD) and from other non-acceptable donor lungs (Wierup, P. et al., *Ann Thorac Surg* 2006; 81(2):460-6; and Ingemansson, R. et al., *Ann Thorac Surg* 2009; 87(1): 255-60). This technique is currently under clinical trial for the evaluation and reconditioning of potential donor lungs that under current criteria are not deemed suitable for transplant (Cypel, M. et al., *N Engl J Med* 2011; 364(15): 1431-40). EVLP further offers an opportunity to administer MSCs or MAPCs directly into the donor lung by either intratracheal or intravascular routes prior to implantation. Using this approach the inventors chose to initially assess direct airway MAPC administration into a single lobe with the contralateral lung as comparison to directly assess effects within each individual lung. The cold ischemic storage (8 hours of total cold storage) was prolonged beyond the actual times generally accepted for the lungs to potentiate any IRI that might develop and thus to maximize potential anti-inflammatory actions of the MSCs. The inventors also chose to use "off the shelf" non-HLA matched MAPCs as proof of feasibility. Moreover, the inventors demonstrate a consistent and potent anti-inflammatory effect of the MAPCs. Notably, the change in cytokine profile, particularly increase in IL-10, may be particularly beneficial for IRI.

From the above description of the present invention, those skilled in the art will perceive improvements, changes and modifications. Such improvements, changes, and modifications are within the skill of those in the art and are intended to be covered by the appended claims. All patents, patent applications, and publications cited herein are incorporated by reference in their entirety.

What is claimed is:

1. A method comprising transplanting a tissue that has been exposed ex vivo to exogenous stem cells, wherein the stem cells are non-embryonic, non-germ cells that express telomerase, have a normal karyotype, are not tumorigenic, and wherein the stem cells have undergone at least 10-40 cell doublings in cell culture prior to their exposure to the tissue, wherein the tissue is exposed to the stem cells prior to transplantation into a recipient.

2. The method of claim 1, wherein the stem cells can differentiate into cell types of at least two of endodermal, ectodermal, and mesodermal germ layers.

3. The method of claim 1, wherein the stem cells express oct4.

4. The method of claim 2, wherein the stem cells can differentiate into cell types of endodermal, ectodermal, and mesodermal germ layers.

5. The method of claim 3, wherein the stem cells can differentiate into cell types of at least two of endodermal, ectodermal, and mesodermal germ layers.

6. The method of claim 5, wherein the stem cells can differentiate into cell types of endodermal, ectodermal, and mesodermal germ layers.

7. The method of claim 1, wherein the stem cells are non-HLA matched, allogeneic cells.

8. The method of claim 1, wherein the stem cells have undergone at least 30-35 cell doublings.

9. The method of claim 1, wherein the concentration of stem cells exposed to the tissue is about $1 \times 10^6$ cells/ml to about $10 \times 10^6$ cells/ml.

10. The method of claim 1, wherein the stem cells are exposed to the tissue for about 2-4 hours.

11. The method of claim 1, wherein the stem cells are contained in a fluid for perfusion into the tissue or in a carrier for administration to the tissue.

12. The method of claim 1, wherein the stem cells are contained in a medium in which the tissue is bathed prior to transplantation.

13. The method of claim 1, wherein the tissue is selected from the group consisting of cornea, skin, veins, arteries, bone, tendons and valves.

14. The method of claim 1, wherein exposure to the stem cells reduces inflammation in the tissue.

15. The method of claim 1, wherein exposure to the stem cells reduces the occurrence of inflammatory cells in the tissue.

16. The method of claim 1, wherein exposure to the stem cells reduces inflammatory cytokines in the tissue.

17. The method of claim 1, wherein exposure to the stem cells reduces ischemic-reperfusion injury in the tissue.

18. The method of any of claims 1-17 wherein the stem cells are derived from bone marrow.

19. The method of claim 18 wherein the stem cells are derived from human bone marrow.

* * * * *

SEQUENCE LISTING

<160> NUMBER OF SEQ ID NOS: 32

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
tggtgtcttc agtggatgta ttt        23

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
agtctctcat ctcctcctcc tc        22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
gaatccttcc tctccttgga ac        22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
gccttctccc aagtgcataa        20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
acacatgcta gtggctgaaa        20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
gcatcctctc cctctgaaat ac        22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctggaggac tttaagggtt ac                                              22

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gatgtctggg tcttggttct c                                               21

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctggtgatg ggagttgtat tt                                              22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctgccgccta aagccatatt                                                 20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgggaaccag atgcaagtaa g                                               21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aatgagtgga tttcccgtgt ag                                              22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgcccacatc aaggagtatt t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gatgtactcc cgaacccatt t                                              21

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgtggagctg taccagaaat ac                                             22

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cacaactccg gtgacatcaa                                                20

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtaataactc taccctggca ctataa                                         26

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
catgggaaag gtgagggaaa ta                                             22

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccggaacagc acaagagtta                                               20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtctgtgtta ctggactcct tc                                            22

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggtcaatgtc aagagaggaa gag                                           23

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctagtgagag tcaagcacca atag                                          24

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggtgtgaacc atgagaagta tga                                           23

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gagtccttcc acgataccaa ag                                            22

<210> SEQ ID NO 25
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccaaagaggc ctggaaggaa ta                                              22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtactgcctc tgactggtaa tg                                              22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtcagagtca ccatcctctt tg                                              22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcaagctcat ctccacagta tc                                              22

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
caggttgctt ggctgattat g                                               21

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcaagctcat ctccacagta tc                                              22

<210> SEQ ID NO 31
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cttgaggtca gcctacagat aac                                              23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
acctcccatt ggtgaacata taa                                              23
```